(12) United States Patent
Mohr et al.

(10) Patent No.: US 6,818,649 B2
(45) Date of Patent: Nov. 16, 2004

(54) CHROMENYLMETHYL PYRIMIDINEDIAMINES AS ANTIBACTERIAL AGENTS

(75) Inventors: Peter Mohr, Basle (CH); Philippe Pflieger, Schwoben (FR)

(73) Assignee: Basilea Pharmaceutica AG, Binningen (CH)

( * ) Notice: Subject to any disclaimer, the term of this patent is extended or adjusted under 35 U.S.C. 154(b) by 87 days.

(21) Appl. No.: 10/258,777

(22) PCT Filed: Apr. 20, 2001

(86) PCT No.: PCT/EP01/04541

§ 371 (c)(1),
(2), (4) Date: Oct. 28, 2002

(87) PCT Pub. No.: WO01/83476

PCT Pub. Date: Nov. 8, 2001

(65) Prior Publication Data

US 2003/0144246 A1 Jul. 31, 2003

(30) Foreign Application Priority Data

Apr. 27, 2000 (EP) .............................. 00108945

(51) Int. Cl.[7] ................... C07D 405/06; C07D 405/14; A61K 31/506
(52) U.S. Cl. ..................... 514/275; 544/323; 544/324; 544/325
(58) Field of Search ................ 544/323, 324, 544/325; 514/275

(56) References Cited

U.S. PATENT DOCUMENTS 5,773,446 A 6/1998 Masciadri .................. 514/275

OTHER PUBLICATIONS

Nau et al., PubMed Abstract (Clin Pharmacokinet. 35(3):223–46), Sep. 1998.*
Johnson et al., J. Med. Chem., vol. 32, pp. 1942–1949 (1989).
Roth et al., J. Med. Chem., vol. 32, pp. 1949–1958 (1989).

* cited by examiner

*Primary Examiner*—Deepak Rao

(57) ABSTRACT

This invention is concerned with substituted chromene derivatives of the general formula (I)

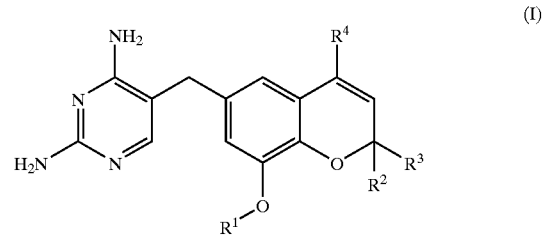

in which $R^1$–$R^4$ are as defined in the specification and claims. The invention further relates to the pharmaceutically acceptable acid addition salts of these compounds, their use as therapeutically active substances; medicaments based on these substances, optionally in combination with sulphonamides, and their production; the use of these substances as medicaments and for the production of antibacterially-active medicaments; as well as the manufacture of the compounds of formula (I) and their pharmaceutically acceptable acid addition salts and intermediates for their manufacture.

11 Claims, No Drawings

CHROMENYLMETHYL PYRIMIDINEDIAMINES AS ANTIBACTERIAL AGENTS

This invention is concerned with substituted chromene derivatives of the general formula

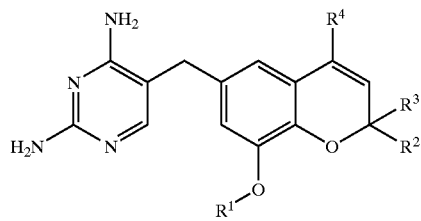

I in which
R¹ represents alkyl or cycloalkylalkyl,
R² and R³ each independently represent alkyl or cycloalkyl or taken together with the adjacent carbon atom represent a saturated 3- to 6-membered carbocyclic or heterocyclic ring, the alkyl, cycloalkyl, carbocyclic or heterocyclic ring being unsubstituted or substituted, and
R⁴ represents hydrogen, halogen, cyano, alkyl, alkylthio, alkenyl, alkynyl, hydroxyalkyl, hydroxyalkynyl, alkoxyalkyl, alkoxyalkynyl, trialkylsilyl, aryl or heteroaryl,
and pharmaceutically acceptable acid addition salts of these compounds.

The above compounds are novel and possess valuable antibiotic properties. They can be used in the control and prevention of infectious diseases. In particular, they exhibit a pronounced antibacterial activity, including against multi-resistant gram-positive strains, such as *Streptococcus pneumoniae* and *Staphylococcus aureus*. These compounds can also be administered in combination with known antibacterially active substances and then exhibit a synergistic effect. Typical combination partners are e.g. sulphonamides, which can be admixed with the compounds of formula I or their salts in various ratios.

Objects of the present invention are compounds of formula I and their pharmaceutically acceptable acid addition salts per se and their use as therapeutically active substances; medicaments based on these substances, optionally in combination with sulphonamides, and their production; the use of these substances as medicaments and for the production of antibacterially-active medicaments; as well as the manufacture of the compounds of formula I and their pharmaceutically acceptable acid addition salts and intermediates for their manufacture.

The groups named above are defined below. In combined residues such as hydroxyalkyl, cycloalkylalkyl etc. the exemplification is to be understood accordingly.

The term "halogen" means fluorine, chlorine, bromine or iodine, preferably fluorine, chlorine or bromine.

The term "alkyl" denotes a straight or branched chain hydrocarbon group which carries up to and including 6, preferably 4 carbon atoms, if not otherwise specified. Examples are, e.g., methyl, ethyl, n-propyl, isopropyl, isobutyl, sec-butyl, t-butyl. The alkyl group being optionally substituted, e.g., by halogen (e.g. chlorine, bromine, fluorine); cyano; lower alkoxy (e.g. methoxy, n-butoxy); nitro; amino; lower alkoxycarbonylamino (e.g. t-butoxycarbonylamino); lower alkanoylamino (e.g. acetylamino).

The term "alkoxy" and "alkylthio" denote groups wherein the alkyl part is as defined above and which are attached via an oxygen or sulfur atom, respectively, examples of such groups are methoxy, ethoxy, n-propoxy, isopropoxy, isobutoxy, sec-butoxy, t-butoxy; and methylthio, ethylthio, n-propylthio, isopropylthio, isobutylthio, sec-butylthio, t-butylthio.

"Alkenyl" and "alkynyl" are unsaturated straight or branched chain hydrocarbon groups which carry up to and including 6, preferably 4 carbon atoms having at least one double or triple bond, respectively, e.g. vinyl, 2-propenyl, 2,4-butadienyl, isopropenyl; 1-propynyl, 2-propynyl, 1-butynyl, 3-butynyl. These groups may be unsubstituted or substituted. Examples of substituted alkynyl groups are, e.g., 3-hydroxy-1-propynyl, 3-hydroxy-1-butynyl, 3-methoxy-1-propynyl.

"Cycloalkyl" denotes a saturated carbocyclic group which carries 3 to 6 carbon atoms, e.g., cyclopropyl, cyclobutyl, cyclopentyl, cyclohexyl. The cycloalkyl group being optionally substituted, e.g., by halogen (e.g. chlorine, bromine, fluorine); cyano; lower alkoxy (e.g. methoxy, n-butoxy); nitro; amino; lower alkoxycarbonylamino (e.g. t-butoxycarbonylamino); lower alkanoylamino (e.g. acetylamino).

"Cycloalkylalkyl" denotes the combination of cycloalkyl and alkyl as defined above, e.g., cyclopropylmethyl, 2-cyclopropylethyl, cyclopentylmethyl.

"Carbocyclic rings" (formed with R² and R³) are saturated and contain 3 to 6 carbon atoms, e.g. cyclopropyl, cyclobutyl, cyclopentyl, cyclohexyl. This carbocyclic group being optionally substituted, e.g., by halogen (e.g., chlorine, bromine, fluorine); cyano; lower alkoxy (e.g. methoxy, n-butoxy); nitro; amino; lower alkoxycarbonylamino (e.g. t-butoxycarbonylamino); lower alkanoylamino (e.g. acetylamino).

Heterocyclic rings (formed with R² and R³) refer to heterocyclic, saturated 3 to 6 membered rings containing one or two heteroatoms selected from nitrogen, oxygen and sulfur, e.g. aziridinyl, oxiranyl, thiiranyl, azetidinyl, oxetanyl, thietanyl, pyrrolidinyl, tetrahydrofuryl, tetrahydrothienyl, piperidyl, tetrahydropyranyl, tetrahydrothiopyranyl, morpholinyl, thiomorpholinyl, piperazinyl, dioxolanyl, imidazolidinyl, oxazolidinyl, isoxazolidinyl, thiazolidinyl, pyrazolidinyl, etc. These rings may be further substituted, e.g. by t-butoxycarbonyl.

"Aryl" denotes phenyl or naphthyl groups which can optionally be substituted e.g. by halogen (e.g. chlorine, bromine, fluorine); cyano; lover alkoxy (e.g. methoxy, n-butoxy); nitro; amino; lower alkoxycarbonylamino (e.g. t-butoxycarbonylamino); lower alkanoylamino (e.g. acetylamino).

"Heteroaryl" denotes 5- or 6-membered heteroaromatic groups which contain one or more rings and which have 5–9 carbon atoms and 1–4 hetero atoms, preferably N, O and/or S. Examples of such rings are for example furyl, pyranyl, thienyl, pyrrolyl, pyrazolyl, imidazolyl, triazolyl, tetrazolyl, oxazolyl, oxadiazolyl, isoxazolyl, thiazolyl, isothiazolyl, pyridyl, pyridazinyl, pyrimidinyl, pyrazinyl and triazinyl. These groups can also be fused preferably to a phenyl ring, e.g. benzopyranyl, benzofuranyl, indolyl and quinolinyl. The "heteroaryl groups" are unsubstituted or substituted by halogen (e.g. chlorine, bromine, fluorine); cyano; lower alkoxy (e.g. methoxy, n-butoxy); nitro; amino; lower alkoxycarbonylamino (e.g. t-butoxycarbonylamino); lower alkanoylamino (e.g. acetylamino).

Preferred compounds of formula I are:

5-(4-Bromo-8-methoxy-2,2-dimethyl-2H-chromen-6-ylmethyl)-pyrimidine-2,4-diamine, 5-[(4-bromo-2',3',5',6'-tetrahydro-8-methoxyspiro[2H-1-benzopyran-2,4'-[4H]pyran]-6-yl)-methyl]-2,4-pyrimidinediamine, 5-(8-ethoxy-2,2,4-trimethyl-2H-chromen-6-ylmethyl)-pyrimidine-2,4-diamine, 5-(4-chloro-8-methoxy-2,2-dimethyl-2H-chromen-6-ylmethyl)-pyrimidine-2,4-diamine, 5-(8-ethoxy-4-ethyl-2,2-dimethyl-2H-chromen-6-ylmethyl)-pyrimidine-2,4-diamine, 5-(8-methoxy-2,2-dimethyl-4-methylsulfanyl-2H-chromen-6-ylmethyl)-pyrimidine-2,4-diamine, 5-(8-ethoxy-2,2-dimethyl-4-propyl-2H-chromen6-ylmethyl)-pyrimidine-2,4-diamine, 5-[8-methoxy-4-(3-methoxy-prop-1-ynyl)-2,2-dimethyl-2H-chromen-6-ylmethyl]-pyrimidine-2,4-diamine, 5-[4-(4-fluoro-phenyl)-8-methoxy-2,2-dimethyl-2H-chromen-6-ylmethyl]-pyrimidine-2,4-diamine, 5-[(4-bromo-8-ethoxyspiro[2H-1-benzopyran-2,1'-cyclobutan]-6-yl)methyl]-2,4-pyrimidinediamine, 5-(4-bromo-8-ethoxy-2,2-dimethyl-2H-chromen-6-ylmethyl)-pyrimidine-2,4-diamine and their pharmaceutically acceptable acid addition salts.

The compounds of formula I form pharmaceutically acceptable acid addition salts with organic and inorganic acids. Examples of acid addition salts of compounds of formula I are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkyl- and arylsulphonic acids such as methanesulphonic acid, p-toluenesulphonic acid, benzenesulphonic acid and the like as well as salts with organic carboxylic acids, for example with acetic acid, tartaric acid, maleic acid, citric acid, benzoic acid, salicyclic acid, ascorbic acid and the like.

The compounds of formula I and their pharmaceutically acceptable acid addition salts can be manufactured by methods known in the art, especially in accordance with the invention by a) reacting a compound of the general formula

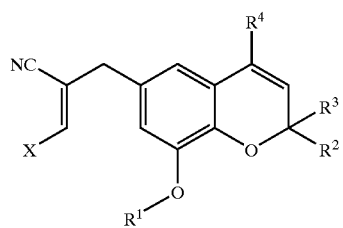

in which $R^1$–$R^4$ have the above significance, X represents a leaving group, and any functional group thereon being optionally protected, with guanidine and cleaving off any protecting group present, or b) for the manufacture of compounds of formula I in which $R^4$ is other than hydrogen or halogen reacting a compound of the general formula

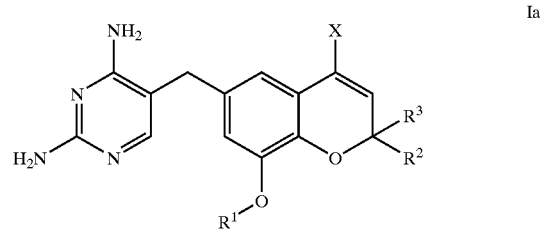

with a compound of the general formula $$R^{40}Y \qquad \text{III}$$

in which $R^1$–$R^3$ have the above significance, $R^{40}$ is as $R^4$ except hydrogen and halogen, any functional group in $R^1$–$R^3$ and $R^{40}$ being optionally protected, one of the symbols X and Y represents a leaving group and the other represents a group which is eliminated with this leaving group, and cleaving off any protecting group present, or c) converting a compound of formula I into a pharmaceutically acceptable acid addition salt.

The cyclization of the starting materials of formula II (where the =CHX group can be either in (E)- or (Z)-configuration) with guanidine or a salt thereof in accordance with variant a) of the process in accordance with the invention is preferably carried out in an inert organic solvent, preferably in a lower alkanol, e.g. ethanol, or in dimethyl sulphoxide, tetrahydrofuran or dioxan, and at about 50 to 100° C. The guanidine is preferably used as a salt, e.g. as the hydrochloride, in which case the reaction is preferably carried out in the presence of a base, e.g. potassium t-butylate. In formula II the leaving group X is preferably bromine, iodine, methylsulfonyloxy, trifluoromethylsulfonyloxy, phenylsulfonyloxy or p-tolylsulfonyloxy.

In the reaction of the compounds Ia and III in accordance with variant b) of the process in accordance with the invention there are to be understood under eliminating groups leaving groups X and, respectively, Y which react with one another and accordingly both "eliminate" with the formation of an eliminating byproduct. Many possibilities present themselves to a person skilled in the art in this respect; the following embodiments are mentioned as examples:

X=bromine, iodine, methanesulfonyloxy, trifluoromethanesulfonyloxy, phenylsulfonyloxy, p-tolylsulfonyloxy;

Y=(OH)$_2$B—.

This reaction with a boronic acid derivative III, also known as a "Suzuki coupling", is preferably effected in an inert organic solvent such as e.g. dioxane, tetrahydrofuran or dimethyl sulfoxide at a temperature between about 20° C. and the boiling point of the reaction mixture. A base such as an alkali metal carbonate, e.g. potassium carbonate, is preferably added as well as a catalyst, preferably a palladium complex such as tetrakis-(triphenylphosphine)-palladium.

A metal compound with Y=—Sn(lower-alkyl)$_3$, e.g. —Sn(CH$_{33}$ or —Sn(n-butyl)$_3$ ("Stille reaction"); —MgHal ("Grignard coupling"); or —ZnHal and Hal=bromine or iodine can be used in the above reaction as the reaction partner III. No base is used in this reaction, although the catalyst described above is preferably used. It can also be advantageous to add an inert salt, especially lithium chloride.

The aforementioned reaction can also be carried out with interchanged substituents X and Y, e.g. with X=—Sn(CH$_3$)$_3$, —MgHal or —ZnHal and Y=bromine, iodine, methanesulfonyloxy, trifluoromethanesulfonyloxy, phenylsulfonyloxy, p-tolylsulfonyloxy. The reaction conditions are essentially the same.

Functional groups, such as amino groups, should be protected. A suitable protecting group for amino is e.g. t-butoxycarbonyl. Such group can be split off (cf. Example 24) hydrolytically with acid treatment, e.g. trifluoroacetic acid, or mineral acid such as hydrochloric acid, in an organic solvent e.g. methylene chloride or chloroform.

The manufacture of the acid addition salts of the compounds of formula I in accordance with variant c) can be effected in a manner known per se, e.g. by reacting a compound of formula I with an equivalent amount of the desired acid, conveniently in a solvent such as water or in an organic solvent such as ethanol, methanol or acetone. The temperature at which the salt formation is carried out is not critical. It generally lies at room temperature, but can also readily be lower or higher, for example in the range of 0° C. to +50° C.

Compounds of formula I can be prepared by elaborating an aldehyde of formula IV optionally protected, according to known procedures by reacting it first with 3-anilinopropionitrile in the presence of a base, preferably KOtBu, and then heating the intermediate with an excess of guanidine hydrochloride and base, preferably KOtBu, in ethanol.

IV

[structure of IV]

a] If R$^4$=aryl or heteroaryl
the intermediate IV can be synthesized by coupling either free aldehyde IVa or a corresponding acetal V with an aryl- or heteroaryl boronic acid IVa

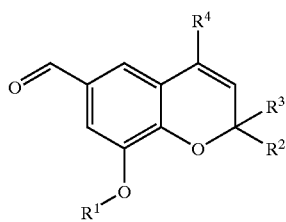

according to typical "Suzuki-conditions" (as in the above variant b) in an inert organic solvent like dimethylformamide, tetrahydrofuran, dioxane or dimethoxyethane at a temperature between 20° and the boiling point of the reaction mixture in the presence of a base, preferably K$_3$PO$_4$ or Na$_2$CO$_3$, and a Pd-catalyst, preferably Pd(Ph$_3$P)$_4$.

A convenient variant generates the Suzuki-reagent in situ by reacting an aryl- or heteroaryl bromide or iodide with 4,4,5,5,4',4',5',5'-octamethyl[2,2']bi[[1,3,2]dioxa-borolanyl] in the presence of a Pd-catalyst, preferably PdCl$_2$(dppf), and KOAc in DMF (*Tetrahedron Letters* 1997, 3841).

b] If R$^4$=alkynyl
the intermediate IV can be synthesized by coupling either free aldehyde IVa or a corresponding acetal V with an alkyne according to typical Sonogashira-conditions, i.e. a Pd-catalyst, e.g. (Ph$_3$P)$_2$PdCl$_2$ or Pd(Ph$_3$P)$_4$, a copper salt like CuI, and a base like triethylamine or piperidine, without solvent or in an inert solvent like dimethylformamide.

c] If R$^4$=alkyl, trialkylsilyl, alkylthio, or hydroxyalkyl
the intermediate IV can be synthesized by subjecting compound V to a metal/halogen-exchange with nBuLi or tBuLi and reacting the resultant derivative VI with an electrophile, i.e. an alkyl halide, tosylate or trifluoromethanesulfonate, a trialkylsilyl halide, a dialkyl disulfide, or an aldehyde or ketone.

VI

[structure of VI]

d] If R$^4$=Cl
the intermediate IV can be synthesized by reacting the above prepared derivative VI with mesyl-Cl as electrophile, yielding, after cleavage of the acetal, the corresponding compound IV with R$^4$=Cl.

Intermediate V is derived from intermediate IVa by treatment with Me$_3$OSiCH$_2$CH$_2$OSiMe$_3$ at −78° in CH$_2$Cl$_2$ and trifluoromethanesulphonic acid trimethylsilyl ester as catalyst (*Tetrahedron Letters* 1980, 1357).

Intermediate IVa is synthesized from intermediate IVb by a bromination-dehydro-bromination-sequence involving treatment with Br$_2$ in CH$_2$Cl$_2$ at −78° followed by DBN- or DBU-induced elimination of HBr in an inert solvent like tetrahydrofuran.

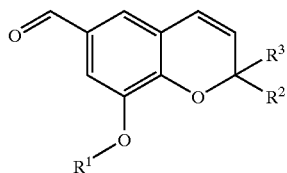
IVb

Aldehyde IVb is available by a Heck-type-reaction-ring closure according to literature precedents using iodo-phenol VII and vinyl-alcohol VIII in the presence of a Pd-catalyst like Pd(POAc)$_2$ and a base like NaHCO$_3$ in an inert solvent like dimethylformamide (Tetrahedron Letters 1991, 7739).

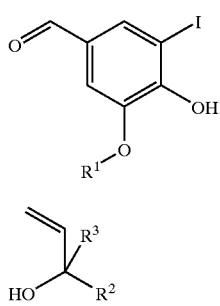
VII

VIII

Iodo-phenol VII is available by iodination of IX according to standard conditions (N-iodo-succinimide in acetonitrile); the latter can be prepared by mono-alkylation of 3,4-dihydroxy-benzaldehyde X involving deprotonation with a base, preferably NaH in dimethylformamide, followed by reaction with an alkyl bromide or iodide.

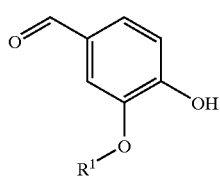
IX

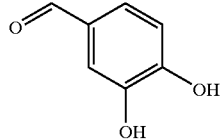
X

The illustrative synthetic schemes follow below.

Building Up of the Ring System

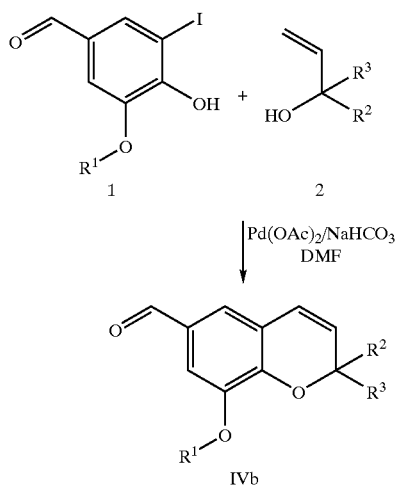

wherein the symbols are as defined above.

Functionalization and Protection

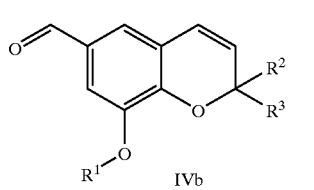
IVb $\xrightarrow{\text{Br}_2}{-78°}$

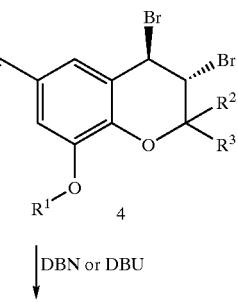
4

↓ DBN or DBU

-continued
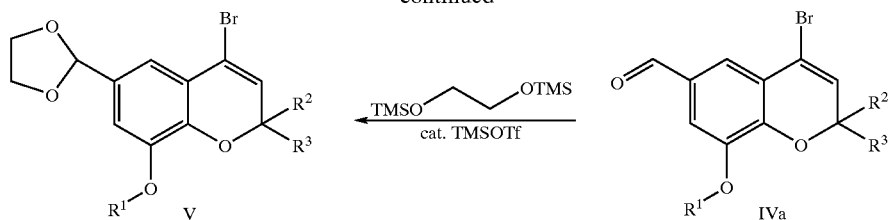
Suzuki-coupling
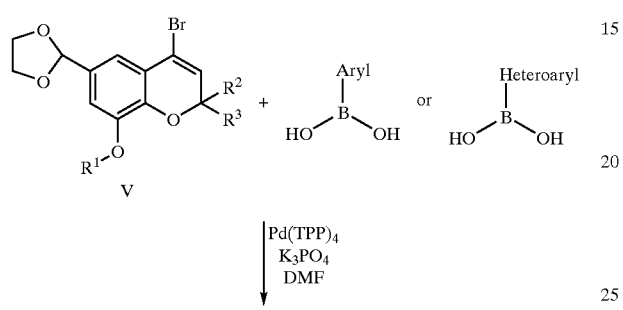
Variants Involve a] Suzuki Coupling with Free Aldehyde or b] with In Situ Generated Pinacol-derived Boronic Ester
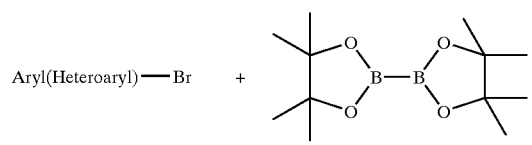
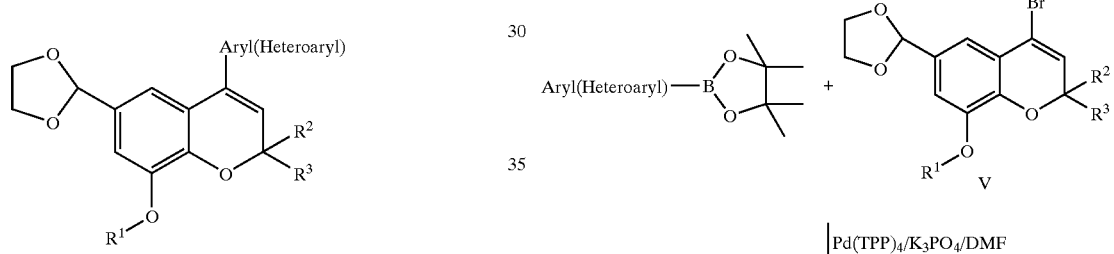
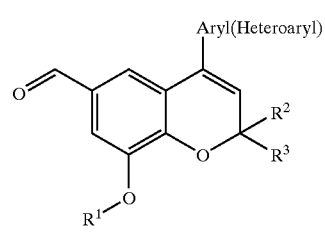
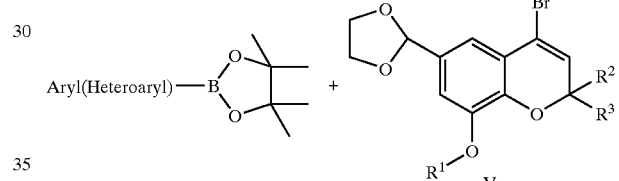
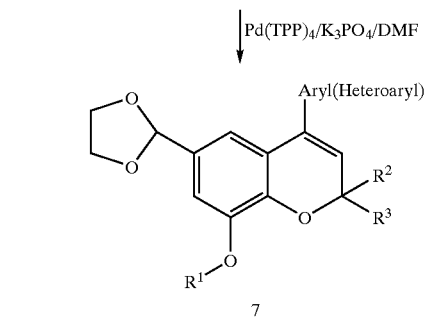
Functionalization Via Metal/Halogen-Exchange
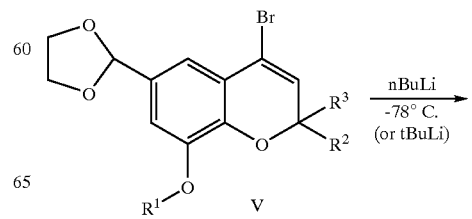
The symbols are as defined above.
The above-mentioned procedure can be applied for the cleavage of the aldehyde protecting group of compounds 10–17.

11
-continued
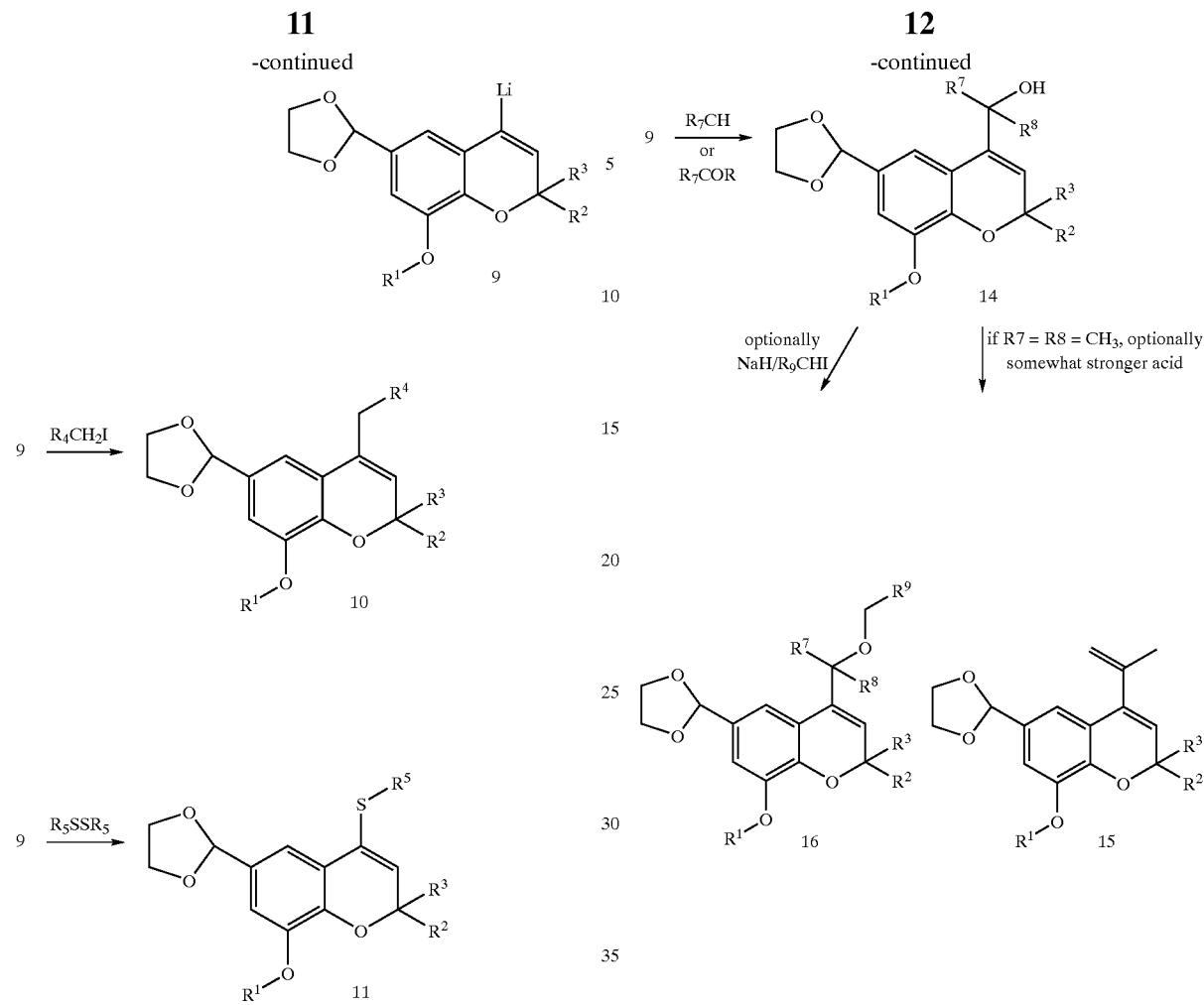
12
-continued
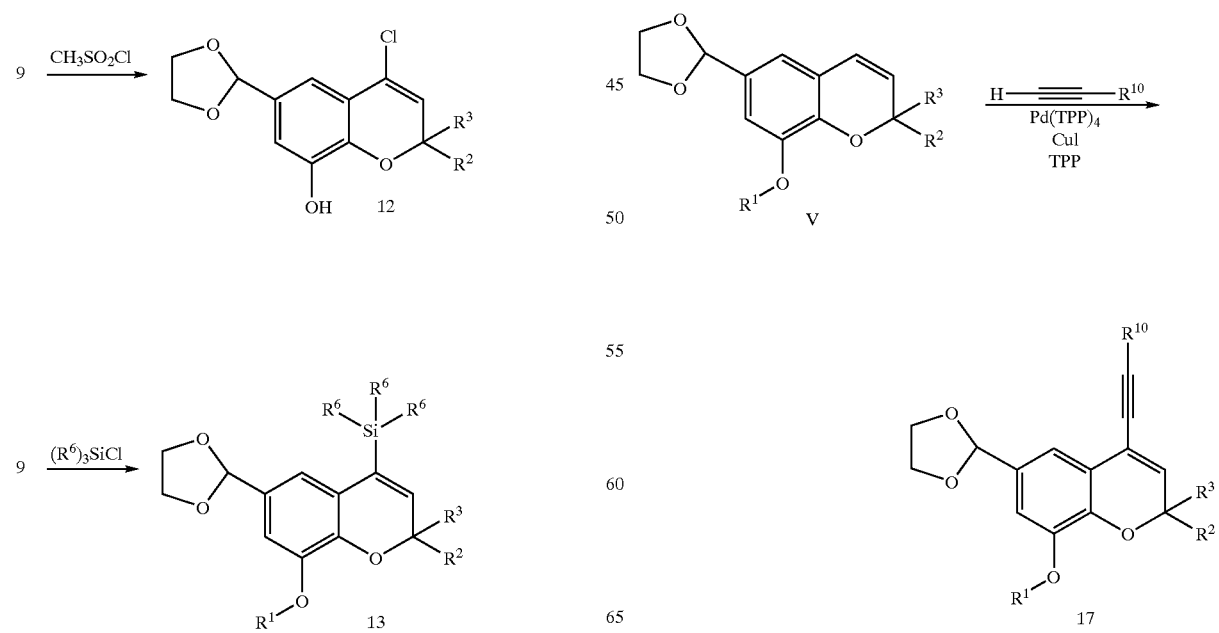
Functionalization Via Sonogashira-coupling Elaboration of the Final Product

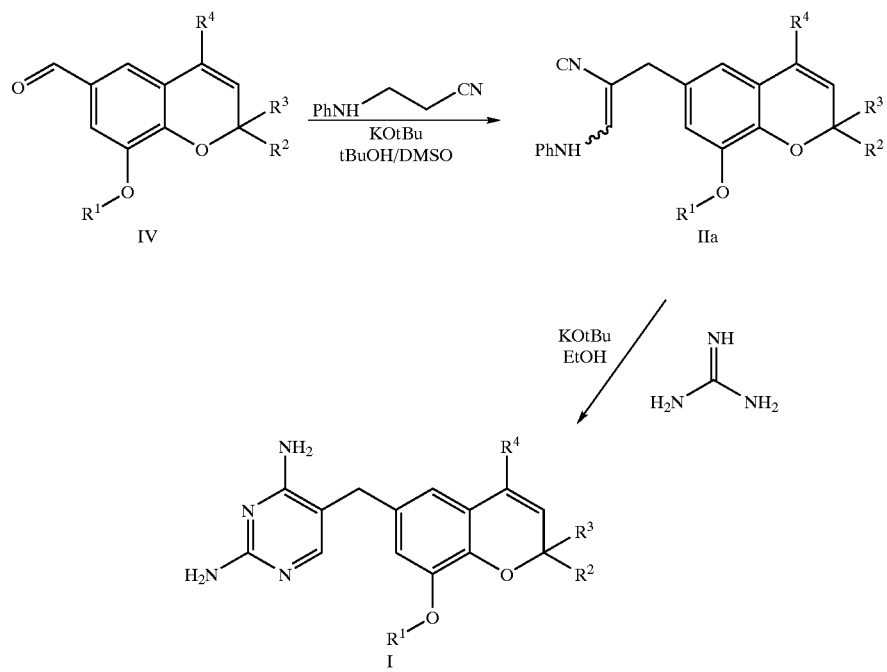

the symbols used in the above schemata are as defined above.

The abbreviations have the meanings given below:

TMS=trimethylsilyl
TMSOTf=trifluoromethanesulphonic acid trimethylsilyl ester
DBN=1,5-diazabicyclo[4.3.0]non-5-ene
DBU=1,8-diazabicyclo[5.4.0]undec-7-ene
TPP=triphenylphosphin(yl)
DMF=dimethylformamide
Bu=butyl
$R^5$–$R^9$=alkyl
$R^{10}$=alkyl, hydroxyalkyl, alkoxyalkyl, trialkylsilyloxyalkyl
DMSO=dimethylsulfoxide
Ph=phenyl
EtOH=ethanol As mentioned earlier, the compounds of formula I and their pharmaceutically acceptable salts possess valuable antibacterial properties. They are active against a large number of pathogenic microorganisms such as e.g. *Staphylococcus areus, Streptococcus pneumoniae* etc. by virtue of their action in inhibiting bacterial dihydrofolate reductase (DHFR).

The inhibition of the enzyme was taken as a measurement for the antibacterial activity. It is determined using the method of Baccanari and Joyner (Biochemistry 20, 1710 (1981)); see also P. G. Hartman et al., FEB 242,157–160 (1988).

The $IC_{50}$ values (concentration at which the enzyme is inhibited to 50%) are determined graphically.

The following Table contains inhibitory concentrations determined in the above test for representative members of the class of compound defined by formula I. The following microorganisms were tested:

Col. 1: MIC Spn1/1; µg/ml (*Streptococcus pneumoniae* 1/1, Trimethoprim- and Penicillin-resistant, Serotype 6; clinical isolate, stored at −80° C.)

Lit.: H. Locher et al., Can. J. Infect. Dis.6: Suppl. C, p 469C.

Col. 2: MIC Sa101; µg/ml (*Staphylococcus aureus* 101, MRSA[*])— and Trimethoprim-resistant; clinical isolate, stored at −80° C.)

Lit.: A. Burdeska et al., FEBS 266:159–162, 1999; G. Dale et al., J. Mol. Biol. 266:23–30, 1997.

Col. 3: DHFR Spn1/1; µM—the $IC_{50}$-values in µM against the purified DHFR of the above strain Sp1/1 of *Streptococcus pneumoniae*.

Col. 4: DHFR Sa1; µM—the $IC_{50}$-values in µM against the purified DHFR of the strain 157/4696 (highly trimethoprim-resistant; clinical isolate) of *Staphylococcus aureus*

Lit.: A. Burdeska et al., FEBS 266:159–162, 1999; G. Dale et al., J. Mol. Biol. 266:23–30, 1997.

[*]) MRSA=Methicillin Resistant *Staphylococcus Aureus*

TABLE

| Example No. | MIC Spn1/1 µg/ml | MIC Sa101 µg/ml | DHFR Spn1/1 µM | DHFR Sa1 µM |
|---|---|---|---|---|
| 2 | 4 | 1 | 0.052 | 0.15 |
| 21 | 4 | 1 | 0.052 | 0.15 |
| 8 | 2 | 4 | 0.015 | 1.3 |
| 6 | 4 | 1 | 0.11 | 0.38 |
| 9 | 1 | 4 | 0.012 | 0.67 |
| 4 | 4 | 2 | 0.078 | 0.088 |
| 10 | 2 | 4 | 0.015 | 1.1 |
| 16 | >8 | 4 | 0.68 | 0.22 |
| 32 | >8 | >8 | 0.19 | 0.08 |
| 30 | 4 | 2 | 0.0089 | 0.21 |
| 7 | 0.5 | 0.5 | 0.00033 | 0.11 |
| Trimethoprim | >32 | 32 | 3.1 | 19 |
| Epiroprim | 4 | 16 | 0.19 | 2 |

The products in accordance with the invention can be used as medicaments, e.g. in the form of pharmaceutical preparations for enteral or parenteral administration. The products in accordance with the invention can be administered, for example, perorally, e.g. in the form of tablets, coated tablets, dragées, hard and soft gelatine capsules, solutions, emulsions or suspensions, rectally, e.g. in the form of suppositories, or parenterally, e.g. in the form of injection solutions. The invention thus also relates to a method of prophylaxis and treatment of infectious diseases which comprises administering a compound of formula I alone or in combination with a sulphonamide.

The production of the pharmaceutical preparations can be effected in a manner which will be familiar to any person skilled in the art by bringing the substances in accordance with the invention, if desired in combination with other therapeutically valuable substances, into a galenical administration form together with suitable, non-toxic, inert, therapeutically compatible solid or liquid carrier materials and, if desired, the usual pharmaceutical adjuvants.

Not only inorganic carrier materials, but also organic carrier materials are suitable as such carrier materials. Thus, lactose, corn starch or derivatives thereof, talc, stearic acid or its salts can be used, for example, as carrier materials for tablets, coated tablets, dragées and hard gelatine capsules. Suitable carriers for soft gelatine capsules are, for example, vegetable oils, waxes, fats and semi-solid and liquid polyols (depending on the nature of the active substance no carriers are, however, required in the case of soft gelatine capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, flavorants, salts for varying the osmotic pressure, buffers, coating agents and antioxidants come into consideration as pharmaceutical adjuvants.

For parenteral administration the compounds of formula I and, respectively their salts are preferably provided as lyophilizates or dry powders for dilution with conventional carriers such as water or isotonic saline.

As already mentioned, the compounds of formula I and their salts have antibacterial activity. They inhibit bacterial dihydrofolate reductase and potentiate the antibacterial activity of sulphonamides such as e.g. sulfisoxazole, sulfadimethoxine, sulfamethoxazole, 4-sulphanilamido-5,6-dimethoxy-pyrimidine, 2-sulphanilamido-4,5-dimethyl-pyrimidine or sulfaquinoxaline, sulfadiazine, sulfamonomethoxine, 2-sulphanilamido-4,5-dimethyl-isoxazole and other inhibitors of enzymes which are involved in folic acid biosynthesis, such as e.g. pteridine derivatives.

Oral, rectal and parenteral administration come into consideration for the treatment of hosts, especially warm-blooded hosts, e.g., in human medicine, with the compounds of formula I or combinations thereof with sulphonamides. A daily dosage of about 0.2 g to about 2 g of a compound of formula I in accordance with the invention comes into consideration for adults. When administered in combination with antibacterial sulphonamides the ratio of compound I to sulphonamide can vary within a wide range; it amounts to e.g. between 1:40 (parts by weight) and 1:1 (parts by weight); 1:10 to 1:2 are preferred ratios. Thus, e.g. a tablet can contain 80 mg of a compound I in accordance with the invention and 400 mg of sulfamethoxazole, a tablet for children can contain 20 mg of a compound I in accordance with the invention and 100 mg of sulfamethoxazole; syrup (per 5 ml) can contain 40 mg of compound I and 200 mg of sulfamethoxazole.

The compounds of formula I are characterized by a high antibacterial activity and, respectively, a pronounced synergistic effect in combination with sulphonamides and good tolerance.

The following Examples illustrate the invention. The temperatures are given in degrees Celsius.

EXAMPLE 1 a] 8-Methoxy-2,2-dimethyl-2H-chromene-6-carbaldehyde 3.00 g of 5-iodo-vanilline (10.8 mmol), 3.63 g of $NaHCO_3$ (43.2 mmol), 242 mg of Pd(OAc)2 (1.08 mmol), and 2.79 g of 2-methyl-but-3-en-2-ol (32.4 mmol) were mixed together under argon atmosphere in 21.5 ml of abs. DMF (dimethylformamide) and heated for 2 hours to 120°. The reaction mixture was cooled down to room temperature, poured onto crushed ice, extracted twice with EtOEt (diethyl ether), washed with brine, dried over magnesium sulfate and evaporated to dryness. Flash chromatography ($SiO_2$ with n-hexane/AcOEt (ethyl acetate)=82/18) yielded 1.16 g of the title compound as off-white solid, mp. 87–88°.

b] 4-Bromo-8-methoxy-2,2-dimethyl-2H-chromene-6-carbaldehyde 7.05 g of 8-methoxy-2,2-dimethyl-2H-chromene-6-carbaldehyde (32.3 mmol) were dissolved in 110 ml of $CH_2Cl_2$ and cooled down to −78°. A solution of 7.74 g of $Br_2$ (48.5 mmol) in 20 ml of $CH_2Cl_2$ was added dropwise and stirring continued for 45 min. Pouring onto crushed ice, twofold extraction with ether, washing with brine, drying over magnesium sulfate and evaporation of the solvents left the corresponding trans-dibromide which was used crude for the next step.

The above prepared trans-dibromide was dissolved in 90 ml of abs. THF (tetra-hydrofuran) and treated at 0° with 11.9 g of DBN (96 mmol). The reaction mixture was kept for 1 hour at room temperature and then quenched by pouring onto crushed ice. Extraction with EtOEt, washing with water and brine, drying over magnesium sulfate and evaporation of the solvents left a crude product which was purified by flash chromatography ($SiO_2$ with n-hexane/AcOEt=85/15) to yield 9.23 g of the title compound as white solid.

MS: $(M)^+$ 296, 298, $(M-CH_3)^+$ 281, 283.

c] 4-Bromo-6-[1,3]dioxolan-2-yl-8-methoxy-2,2-dimethyl-2H-chromene 477 mg of 4-bromo-8-methoxy-2,2-dimethyl-2H-chromene-6-carbaldehyde (1.61 mmol) and 365 mg of 1,2-bis-(trimethylsilyloxy)ethane (1.77 mmol) were dissolved under argon atmosphere in 2 ml of abs. $CH_2Cl_2$ and cooled down to −78°. 17.8 mg of trifluoromethanesulphonic acid trimethylsilyl ester (5 mol %) were added via syringe and the reaction allowed to proceed for 2 hours. The reaction was quenched by adding 32 μl of pyridine before pouring the whole mixture onto crushed ice/$NaHCO_3$. Twofold extraction with ether, washing with water, drying over magnesium sulfate and evaporation of the solvents left a crude product which was purified by flash chromatography ($SiO_2$ with n-hexane/AcOEt=8/2) to yield 366 mg of the title compound as a colourless oil, 97% pure according to gas chromatography. Since the acetal is not perfectly stable on $SiO_2$, it is often advantageous to use the crude product for the following steps.

MS: $(M)^+$ 340, 342, $(M-CH_3)^+$ 325,327, $(M-CH_3-C_2H_4O)^+$ 281, 283. NMR: (DMSO, 1H, δ, TMS) 1.40 (s, 6H), 3.78 (s, 3H), 3.9–4.0 (m, 2H), 4.0–4.1 (m, 2H), 5.66 (s, 1H), 6.32 (s, 1H), 7.03 (2×br s, 2×1H).

d] 8-Methoxy-2,2,4-trimethyl-2H-chromene-6-carbaldehyde 360 mg of 4-bromo-6-[1,3]dioxolan-2-yl-8-methoxy-2,2-dimethyl-2H-chromene (1.06 mmol) was dissolved in 4 ml of abs. THF and treated at −78° with 0.816 ml of n-butyl lithium (1.5M, n-hexane, 1.2 eq.). 15 -min. later, 0.131 ml of methyl iodide (2 eq.) were added via syringe and the cooling bath removed after 10 min. After additional 30 min. the reaction mixture was poured onto crushed ice/AcOEt, the organic layer washed with water and brine, dried over magnesium sulfate and evaporated to dryness. The crude product, 86% pure according to gas chromatography, was hydrolyzed as follows:

The above prepared 6-[1,3]dioxolan-2-yl-8-methoxy-2,2,4-trimethyl-2H-chromene was dissolved in 3 ml of THF and treated with 1.5 ml of 3N HCl. After 30 min. at room temperature the reaction mixture was poured onto crushed ice/EtOEt, the organic layer washed with water, dried over magnesium sulfate, and evaporated to dryness. Flash chromatography ($SiO_2$ with n-hexane/AcOEt=15/15) yielded 128 mg of the title compound as colourless oil, 98% pure according to gas chromatography. Fractions containing substantial amounts of 8-methoxy-2,2-dimethyl-2H-chromene-6-carbaldehyde were discarded.

MS: $(M)^+$ 232, $(M-CH_3)^+$ 217. NMR: (DMSO, 1H, δ, TMS) 1.39 (s, 6H), 2.03 (s, 3H), 3.83 (s, 3H), 5.67 (s, 1H), 7.37 (d, J=2, 1H), 7.44 (d, J=2,2H), 9.83 (s, 1H).

e] 5-(8-Methoxy-2,2,4-trimethyl-2H-chromen-6-ylmethyl)-pyrimidine-2,4-diamine

To 125 mg of 8-methoxy-2,2,4-trimethyl-2H-chromene-6-carbaldehyde (0.54 mmol), dissolved in 1.1 ml of abs. DMSO (dimethylsulphoxide) and 0.7 ml of t-butanol, were added 86.5 mg of 3-anilinopropionitrile (1.1 eq.) and 72.5 mg of potassium t-butoxide (1.2 eq.), and the reaction was allowed to proceed for 2.5 hours at ambient temperature. Pouring onto crushed ice, twofold extraction with AcOEt, washing with water and brine, drying over magnesium sulfate and evaporation of the solvents left 194 mg of crude 2-(8-methoxy-2,2,4-trimethyl-2H-chromen-6-ylmethyl)-3-phenylamino-acrylonitrile which was used as such.

The above prepared 194 mg of 2-(8-methoxy-2,2,4-trimethyl-2H-chromen-6-ylmethyl)-3-phenylamino-acrylonitrile were treated with 170 mg of guanidine hydrochloride (3.3 eq.), 199 mg of potassium t-butoxide (3.3 eq.) and 5 ml of ethanol and kept in an oil bath of 80° for 14 hours. The reaction mixture was then poured onto crushed ice, extracted three times with AcOEt, washed with water and brine, dried over magnesium sulfate and evaporated to dryness. Flash chromatography ($SiO_2$ with $CH_2Cl_2$/MeOH/25% $NH_3$=19/1/0.05), followed by crystallisation from EtOEt, yielded 79 mg of the title compound as pale-yellow crystals, mp. 249–250°.

ISP MS: $(M)^+$ 327.4. IR ($cm^{-1}$): 3458, 3447, 3098, 2970, 1656, 1638, 1596, 1560, 1361, 1265, 1121, 1058, 791. NMR: (DMSO, 1H, δ, TMS) 1.31 (s, 6H), 1.91 (s,3H), 3.50 (s,2H),3.70 (s,3H), 5.51 (s, 1H), 5.65 (br s, 2H), 6.05 (br s,2H), 6.70 (d) J=2, 1H), 6.76 (d, J=2, 1H), 7.49 (s, 1H).

EXAMPLE 2

5-(4-Bromo-8-methoxy-2,2-dimethyl-2H-chromen-6-ylmethyl) -pyrimidine-2,4-diamine To 253 mg of 4-bromo-8-methoxy-2,2-dimethyl-2H-chromene-6-carbaldehyde (0.81 mmol, see example 1b]), dissolved in 1.1 ml of abs. DMSO and 0.7 ml of t-butanol were added 125 mg of 3-anilinopropionitrile (1.05 eq.) and 100 mg of potassium t-butoxide (1.1 eq.), and the reaction was allowed to proceed for 3 hours at ambient temperature. Pouring onto crushed ice, twofold extraction with AcOEt, washing with water and brine, drying over magnesium sulfate and evaporation of the solvents left 418 mg of crude 2-(4-bromo-8-methoxy-2,2-dimethyl-2H-chromen-6-ylmethyl)-3-phenylamino-acrylonitrile as yellow foam which was used as such.

The above prepared 418 mg of 2-(4-bromo-8-methoxy-2,2-dimethyl-2H-chromen-6-ylmethyl)-3-phenylamino-acrylonitrile were treated with 248 mg of guanidine hydrochloride (3.3 eq.), 291 mg of potassium-t-butoxide (3.3 eq.) and 16 ml of ethanol and heated under reflux under argon atmosphere for 14 hours. After cooling, the reaction mixture was poured onto crushed ice, extracted twice with AcOEt, washed with water and brine, dried over magnesium sulfate and evaporated to dryness. Flash chromatography ($SiO_2$ with $CH_2Cl_2$/MeOH/25% $NH_3$=19/1/0.05), followed by crystallization from EtOEt afforded 186 mg of the title compound as light-yellow crystals, mp.238–239°.

ISPMS: $(MH)^+$ 391.2, 393.2, $(M-Br)^+$ 311.2. IR ($cm^{-1}$): 3463, 3450, 3083, 1657, 1638, 1596, 1560, 1465, 1352, 1143, 1097, 1000, 792, 732. NMR: ($CDCl_3$, 1H, δ, TMS) 1.48 (s, 6H), 3.65 (s, 2H), 3.79 (s, 3H), 4.54 (br s, 2H) 4.66 (br s, 2H), 6.02 (s, 1H), 6.62 (s, 1H). 6.92 (s, 1H), 7.80 (s, 1H).

EXAMPLE 3

5-(4-Ethyl-8-methoxy-2,2-dimethyl-2H-chromen-6-ylmethyl)-pyrimidine-2,4-diamine was prepared in analogy to example 1, but using in step d] ethyl iodide instead of methyl iodide; yellow crystals of mp. 256–257°.

ISP MS: $(MH)^1$ 340.1, $(M-CH_3)^+$ 325.2. IR ($cm^{-1}$): 3455, 3445, 3105, 2966, 2934, 1654, 1636, 1595, 1558, 1464, 1360, 1122, 1041, 929, 791. NMR: (DMSO, 1H, δ, TMS) 1.04 (t, J=7.5, 3H), 1.31 (s, 6H), 2.31 (q, J=7.5, 2H), 3.50 (s, 2H), 3.70 (s, 3H), 5.47 (s, 1H), 5.65 (br s, 2H), 6.05 (br s, 2H), 6.73 (s, 1H), 7.50 (s, 1H).

EXAMPLE 4

5-(8-Methoxy-2,2-dimethyl-4-methylsulfanyl-2H-chromen-6-ylmethyl)-pyrimidine-2,4-diamine was prepared in analogy to example 1, but using in step d] dimethyl disulfide as electrophile instead of methyl iodide; yellow solid.

ISP MS: $(MH)^+$ 359.2. NMR: (DMSO, 1H, δ, TMS) 1.35 (s, 6H), 2.28 (s, 3H), 3.53 (s, 2H), 3.72 (s, 3H), 5.44 (s, 1H), 5.68 (br s, 2H), 6.06 (br s, 2H), 6.74 (s, 1H), 6.85 (s, 1H), 7.49 (s, 1H).

EXAMPLE 5

[6-(2,4-Diamino-pyrimidin-5-ylmethyl)-8-methoxy-2,2-dimethyl-2H-chromen-4-yl]-methanol was prepared in analogy to example 1, but using in step d] paraformaldehyde as electrophile giving 4-hydroxymethyl-8-methoxy-2,2-dimethyl-2H-chromene-6-carbaldehyde according to the following procedure as light-yellow crystals of mp. 239–240°.

ISP MS: $(MH)^+$ 343.3. NMR: (DMSO, 1H, δ, TMS) 1.34 (s, 6H), 3.48 (s, 2H), 3.69 (s, 3H), 4.21 (d, J=5, 2H), 4.99 (t, J=5, 1H), 5.65 (br s, 2H), 5.69 (s, 1H), 6.05 (br s, 2H), 6.69 (s, 1H), 6.74 (s, 1H), 7.48 (s, 1H).

4-Hydroxymethyl-8-methoxy-2,2-dimethyl-2H-chromene-6-carbaldehyde 360 mg of 4-bromo-6-[1,3]dioxolan-2-yl-8-methoxy-2,2-dimethyl-2H-chromene (1.06 mmol) was dissolved in 3 ml of abs. THF and treated at −78° with 0.817 ml of n-butyl lithium (1.55M, n-hexane, 1.2 eq.). 20 min. later 0.158 mg of paraformaldehyde (5 eq.) were added and the cooling bath removed. After 90 min. at ambient temperature, the reaction mixture was poured onto crushed ice/AcOEt, the organic layer washed with water and brine, dried over magnesium sulfate, and evaporated to dryness to give a yellow oil which was hydrolyzed as follows:
The above prepared (6-[1,3]dioxolan-2-yl-8-methoxy-2,2-dimethyl-2H-chromen-4-yl)-methanol was dissolved in 3 ml of THF and treated at 0° with 1.5 ml of 3N HCl. 60 min. later, the reaction mixture was poured onto crushed ice/AcOEt, the organic layer washed with water and brine, dried over magnesium sulfate and evaporated to dryness. Flash chromatography ($SiO_2$ with n-hexane/AcOEt=1/1) afforded 123 mg of the title compound as colourless, viscous oil.

MS: $(M)^+$ 248, $(M-CH_3)^+$ 233.

EXAMPLE 6

5-(4-Chloro-8-methoxy-2,2-dimethyl-2H-chromen-6-ylmethyl)-pyrimidine-2,4-diamine was prepared in analogy to example. 2, but using 4-chloro-8-methoxy-2;2dimethyl-2H-chromene-6-carbaldehyde instead of 4-bromo-8-methoxy-2,2-dimethyl-2H-chromene-6-carbaldehyde, yellow crystals of mp. 221–222°. The starting compound was synthesized as described below.

ISP MS: $(MH)^+$ 347.4, 349.4. NMR: (DMSO, 1H, δ, TMS) 1.38 (s, 6H), 3.54 (s, 2H), 3.73 (s, 3H), 5.68 (br s, 2H), 6.03 (s, 1H), 6.08 (br s, 2H), 6.83 (d, J=2, 1H), 6.91 (d, J=2, 1H), 7.52 (s, 1H).

4-Chloro-8-methoxy-2,2-dimethyl-2H-chromene-6-carbaldehyde 366 mg of 4-bromo-6-[1,3]dioxolan-2-yl-8-methoxy-2,2-dimethyl-2H-chromene (1.07 mmol) was dissolved in 4 ml of abs. THF and treated at −78° (dry-ice bath) with 0.735 ml n-butyl lithium (1.6M, n-hexane, 1.1 eq.). 15 min. later, 0.114 ml of mesyl chloride (1.1 eq.) was added and the dry-ice bath replaced by an ice-bth. After 30 min. the reaction mixture was poured onto crushed ice/concentrated HCl and vigorously stirred to cleave the acetal. Twofold extraction with ether, washing with NaCl, drying over magnesium sulfate, and evaporation of the solvents left a crude product which was purified by flash chromatography ($SiO_2$ with n-hexane/AcOEt=87/13) to yield 77 mg of the title compound as white crystals.

MS: $(M)^+$ 252, 254, $(M-CH_3)^+$ 237, 239.

EXAMPLE 7 a] 8-Ethoxy-2,2-dimethyl-2H-chromene-6-carbaldehyde 23.28 g of 3-ethoxy-4-hydroxy-5-iodo-benzaldehyde (79.7 mmol), 16.74 g of $NaHCO_3$ (199.3 mmol), 1.789 g of Pd(OAc)2 (7.97 mmol) and 27.46 g of 2-methyl-but-3-en-2-ol (318.8 mmol) were mixed together under argon atmosphere in 160 ml of abs. DMF and heated for 4¼ hours to 120°. The reaction mixture was cooled down to room temperature, poured onto crushed ice, extracted three times with AcOEt, washed with water, dried over magnesium sulfate and evaporated to dryness. Flash chromatography ($SiO_2$ with n-hexane/AcOEt=82/18) yielded 9.01 g of the title compound as white solid, 97% pure according to gas chromatography.

b] 4-Bromo-8-ethoxy-2,2-dimethyl-2H-chromene-6-carbaldehyde 5.00 g of 8-ethoxy-2,2-dimthyl-2H-chromene-6-carbaldehyde (21.5 mmol) was dissolved in 65 ml of methylene chloride and cooled down to −78°. A solution of bromine in methylene chloride (26.6 ml 0.89M, 1.1 eq.) was added dropwise and stirring continued for 45 min. at −78° and for 1 hour at 0°. Pouring onto crushed ice, twofold extraction with ether, washing with water, drying over magnesium sulfate and evaporation of the solvents left the corresponding trans-dibromide which was used crude for the next step.

The above prepared trans-dibromide was dissolved in 187 ml of abs. THF and treated at 0° with 8.02 g of DBN (64.6 mmol). The reaction mixture was kept for 1¾ hours at room temperature and then quenched by pouring onto crushed ice. Extraction with EtOEt, washing with water, drying over magnesium sulfate and evaporation of the solvents left a crude product which was purified by short flash chromatography (SiO2 with n-hexane/AcOEt=85/15) to yield 6.57 g of the title compound as white solid, >99% pure according to gas chromatography.

c] 5-(4-Bromo-8-ethoxy-2,2-dimethyl-2H-chromen-6-ylmethyl)-pyrimidine-2,4-diamine To 212 mg of 4-bromo-8-ethoxy-2,2-dimethyl-2H-chromene-6-carbaldehyde (0.68 mmol) dissolved in 1.1 ml of abs. DMSO and 0.7 ml of t-butanol were added 104.6 mg of 3-anilinopropionitrile (1.05 eq.) and 84.1 mg of potassium t-butoxide (1.1 eq.), and the reaction was allowed to proceed for 3 hours at ambient temperature. Pouring onto crushed ice, twofold extraction with AcOEt, washing with water and brine, drying over magnesium sulfate and evaporation of the solvents left 300 mg of crude 2-(8-bromo-2,2,4-trimethyl-2H-chromen-6-ylmethyl)-3-phenylamino-acrylonitrile, which was used as such.

The above prepared 300 mg of 2-(8-bromo-2,2,4-trimethyl-2H-chromen-6-ylmethyl)-3-phenylamino-acrylonitrile were treated with 214 mg of guanidine hydrochloride (3.3 eq.), 252 mg of potassium t-butoxide (3.3 eq.) and 10 ml of ethanol and kept in an oil bath of 80° for 16 hours. The reaction mixture was then poured onto crushed ice, extracted twice with AcOEt, washed with water and brine, dried over magnesium sulfate and evaporated to dryness. Flash chromatography ($SiO_2$ with $CH_2Cl_2$/MeOH/25% $NH_3$=19/1/0.05) yielded 87 mg of the title compound as pale-yellow crystals, mp. 218–219°.

ISP MS: $(MH)^+$ 405.3, 407.3. NMR: (DMSO, 1H, δ, TMS) 1.28 (t, J=7,3H), 1.37 (s, 6H), 3.53 (s, 2H), 4.00 (q, J=7, 2H), 5.68 (br s, 2H), 6.08 (br s, 2H), 6.25 (s, 1H), 6.80 (d, J=2, 1H), 6.88 (d, J=2, 1H), 7.51 (s, 1H).

EXAMPLE 8

5-(8-Ethoxy-2,2,4-trimethyl-2H-chromen-6-ylmethyl)-pyrimidine-2,4-diamine was prepared in analogy to example 1, but using in step d] 4-bromo-6-[1,3]dioxolan-2-yl-8-ethoxy-2,2-dimethyl-2H-chromene instead of 4-bromo-6-[1,3] dioxolan-2-yl-8-methoxy-2,2-dimethyl-2H-chromene; yellow solid of mp. 216–218°. The starting compound was synthesized as described below.

ISP MS: $(MH)^+$ 341.3. IR $(cm^{-1})$: 3451, 3325, 3106, 2922, 1634, 1596, 1558, 1461, 1437, 1361, 1265, 1209, 1124, 1054, 997,793. NMR:(MSO, 1H, δ, TMS) 1.26 (t, J==7, 3H), 1.31 (s, 6H), 3.49 (s, 2H), 3.97 (q, J=7,2H), 5.51 (s, 1H), 5.65 (br s, 2H), 6.05 (br s, 2H), 6.70 (s, 1H), 6.74 (s, 1H), 7.49 (s, 1H).

4-Bromo-6-[1,3]dioxolan-2-yl-8-ethoxy-2,2-dimethyl-2H-chromene 6.57 g of 4-bromo-8-ethoxy-2,2-dimethyl-2H-chromene-6-carbaldehyde (21.1 mmol) and 5.667 g of 1,2-bis-(trimethylsilyloxy)ethane (27.5 mmol) were dissolved under argon atmosphere in 25 ml of abs. $CH_2Cl_2$ and cooled down to −78°. 235 mg of trifluoromethanesulphonic acid trimethylsilyl ester (5 mol %) were added via syringe and the reaction allowed to proceed for 2 hours. The reaction was quenched by adding 418 μl of pyridine before pouring the whole mixture onto crushed ice/$NaHCO_3$. Twofold extraction with ether, washing with water and brine, drying over magnesium sulfate and evaporation of the solvents left, after high-vacuum-drying for 2 days) 7.94 g of the title compound as off-white solid, 96.5% pure according to gas chromatog raphy. Since the acetal is not perfectly stable on SiO$_2$, it is generally used without further purification.

MS: (M)$^+$ 354, 356, (M-CH$_3$)$^+$ 339, 341.

EXAMPLE 9

5-(8-Ethoxy-4-ethyl-2,2-dimethyl-2H-chromen-6-ylmethyl)-pyrimidine-2,4-diamine was prepared in analogy to example 8, but using in step d] ethyl iodide instead of methyl iodide as electrophile; yellow solid of mp. 222–225° (dec.).

ISP MS: (MH)$^+$ 355.4. NMR: (DMSO, 1H, δ, TMS) 1.05 (t, J=7, 3H), 1.26 (t, J=7, 3H), 1.32 (s, 6H), 2.30 (q, J=7, 2H), 3.49 (s, 2H), 3.97 (q, J=7, 2H), 5.48 (s, 1H), 6.65 (br s, 2H), 6.05 (br s, 2H), 6.73 (br s, 2H), 7.49 (s, 1H).

EXAMPLE 10

5-(8-Ethoxy-2,2-dimethyl-4-propyl-2H-chromen-6-ylmethyl)-pyrimidine-2,4-diamine was prepared in analogy to example 8, but using in step d] 1-iodo-propane instead of methyl iodide as electrophile; yellow solid of mp. 208–209°.
MS: (M)$^+$ 368.3 (M-CH$_3$)$^+$ 353.3.

EXAMPLE 11

5-(8-Ethoxy-4-isobutyl-2,2-dimethyl-2H-chromen-6-ylmethyl)-pyrimidine-2,4-diamine was prepared in analogy to example 8 as pale-yellow solid of mp. 188°. However, step d] was modified as follows:

8-Ethoxy-4-isobutyl-2,2-dimethyl-2H-chromene-6-carbaldehyde 311 mg of freshly purified 4-bromo-6-[1,3]dioxolan-2-yl-8-methoxy-2,2-dimethyl-2H-chromene (0.88 mmol) were dissolved in 3.5 ml of abs. THF and treated at –78° with 2.0 ml t-butyl lithium (1.5M, n-pentane, 3.4 eq.). 10 min. later, 0.805 ml of isobutyl iodide (5 eq.) were added via syringe and the cooling bath removed after 10 min. After additional 60 min. the reaction mixture was poured onto crushed ice/EtOEt, the organic layer washed with water, dried over magnesium sulfate and evaporated to dryness. The crude product, containing according to gas chromatography 40% of desired product and 57% of debromo-derivative, was hydrolyzed as follows:

The above prepared crude 6-[1,3]dioxolan-2-yl-8-ethoxy-4-isobtyl-2,2-dimethyl-2H-chromene was dissolved in 2.5 ml of THF and treated with 1.2 ml of 3N HCl. After 30 min. at 0°, the reaction mixture was poured onto crushed ice/EtOEt, the organic layer washed with water, dried over magnesium sulfate and evaporated to dryness. Flash chromatography (SiO$_2$ with n-hexane/AcOEt=9/1) yielded 83 mg of the title compound as colourless oil, 98% pure according to gas chromatography.

MS: (M)$^+$ 288.2 (M-CH$_3$)$^+$ 273.2.

EXAMPLE 12

5-(8-Ethoxy-2,2-dimethyl-4-trimethylsilanyl-2H1-chromen-6-ylmethyl)-pyrimidine-2,4-diamine was prepared in analogy to example 8, but using in step d] trimethylsilyl chloride instead of methyl iodide as electrophile; yellow solid of mp. 189–190°.

MS: (M)$^+$ 398.3 (M-CH$_3$)$^+$ 383.2.

EXAMPLE 13

[6-(2,4-Diamino-pyrimidin-5-ylmethyl)-8-ethoxy-2,2-dimethyl-2H-chromen-4-yl]-methanol was prepared in analogy to example 5, but starting the sequence with the ethoxy-derivative; yellow solid of mp.187–189°.

ISP MS: (MH)$^+$ 357.3.

EXAMPLE 14 a] 8-Ethoxy-4-(3-hydroxy-prop-1-ynyl)-2,2-dimethyl-2H-chromene-6-carbaldehyde

To 351 mg of 4-bromo-6-[1,3]dioxolan-2-yl-8-ethoxy-2,2-dimethyl-2H-chromene (0.99 mmol), dissolved in 1 ml of piperidine, were added successively 3.8 mg (0.02 eq.) of copper iodide, 5.2 mg (0.02 eq.) of triphenyl phosphine and 11.4 mg (0.01 eq.) of tetrakis-(triphenylphosphine)-palladium. After heating to 80° 463 mg (3.7 eq.) of propargyloxy-trimethylsilane were added within 2 hours in seven portions. 30 min. later the reaction mixture was cooled down and then poured onto crushed ice/HCl, vigorously stirred for 10 min. to cleave the acetal, extracted twice with AcOEt, washed with water, dried over magnesium sulfate and evaporated to dryness. Flash chromatography (SiO$_2$ with n-hexane/AcOEt 7/3) yielded 196 mg of the title compound as colorless oil, 98% pure according to gas chromatography.

MS: (M)$^+$ 286.1 (M-CH$_3$)$^+$ 271.2.

b] 3-[6-(2,4-Diamino-pyrimidin-5-ylmethyl)-8-ethoxy-2,2-dimethyl-2H-chromen-4-yl]-prop-2-yn-1-ol To 196 mg of 8-ethoxy-4-(3-hydroxy-prop-1-ynyl)-2,2-dimethyl-2H-chromene-6-carbaldehyde (0.68 mmol) dissolved in 0.92 ml of abs. DMSO and 0.56 ml of t-butanol were added 110 mg of 3-anilinopropionitrile (1.1 eq.) and 92 mg of potassium t-butoxide (1.2 eq.), and the reaction was allowed to proceed for 3 hours at ambient temperature. Pouring onto crushed ice, twofold extraction with AcOEt, washing with brine, drying over magnesium sulfate and evaporation of the solvents left 273 mg of crude 2-[8-ethoxy-4-(3-hydroxy-prop-1-ynyl)-2,2-dimethyl-2H-chromen-6-ylmethyl]-3-phenyl-amino-acrylonitrile which was used as such.

The above prepared 273 mg of 2-[8-ethoxy-4-(3-hydroxy-prop-1-ynyl)-2,2-dimethyl-2H-chromen-6-ylmethyl]-3-phenyl-amino-acrylonitrile were treated with 208 mg of guanidine hydrochloride (3.3 eq.), 244 mg of potassium t-butoxide (3.3 eq.), and 12 ml of EtOH and kept in an oil bath of 80° for 6½ hours. The reaction mixture was then poured onto crushed ice, extracted twice with AcOEt, washed with water, dried over magnesium sulfate and evaporated to dryness. Flash chromatography (SiO$_2$ with CH$_2$Cl$_2$/MeOH/25% NH$_3$=19/1/0.05) afforded after crystallisation from EtOEt 58 mg of the title compound as pale-yellow crystals, mp. 242–244°.

ISP MS: (MH)$^+$ 381.4. NMR: (DMSO, 1H, δ, TMS) 1.27 (t, J=7, 3H), 1.36 (s, 6H), 3.51 (s, 2H), 3.98 (q, J=7, 2H), 4.28 (d, J=6,2H), 5.32 (t, J=6, 1H), 5.67 (br s, 2H), 6.07 (s, 1H), 6.08 (br s, 2H), 6.79 (d, J=2, 1H), 6.86 (d, J=2, 1H), 7.43 (s, 1H).

EXAMPLE 15

4-[6-(2,4-Diamino-pyrimidin-5-ylmethyl)-8-ethoxy-2,2-dimethyl-2H-chromen-4-yl]-but-3-yn-2-ol was prepared in analogy to example 14, but using in step a] trimethyl-(1-methyl-prop-2-ynyloxy)-silane instead of propargyloxy-trimethylsilane as coupling partner; yellow crystals, mp.218–219°.

ISP MS: (MH)$^+$ 395.3, (M—OH$_2$)$^+$ 377.4. IR (cm$^{-cm-1}$): 3437, 3322, 2977, 2927, 1638, 1596, 1592, 1457, 1436, 1359, 1265, 1209, 1137, 1095, 1061, 998, 793.

EXAMPLE 16

5-[8-Methoxy-4-(3-methoxy-prop-1-ynyl)-2,2-dimethyl-2H-chromen-6-ylmethyl]-pyrimidine-2,4-diamine was prepared in analogy to example 14, but using in step a] the methoxy instead of the ethoxy-derivative as starting material and by methylation of the non-hydrolyzed intermediate propargylic alcohol as described below; pale-yellow crystals, mp. 236–237°.

MS: (MH)$^+$ 380.2, (M-CH$_3$)$^+$ 365.2. NMR: (DMSO, 1H, δ, TMS) 1.36 (s, 6H), 3.31 (s, 3H), 3.53 (s, 2H), 3.73 (s, 3H), 4.29 (s, 2H), 5.68 (br s, 2H), 6.05 (br s, 2H), 6.12 (s, 1H), 6.78 (d, J=2, 1H), 6.86 (d, J=2, 1H), 7.47 (s, 1H).

8-Methoxy-4-(3-methoxy-propyl-1-ynyl)-2,2-dimethyl-2H-chromene-6-carbaldehyde 218 mg of 3-(6-[1,3] dioxolan-2-yl-8-methoxy-2,2-dimethyl-2H-chromen-4-yl)-prop-2-yn-1-ol (0.69 mmol) was dissolved in 1.4 ml of abs. DMF and treated at 0° with 43 mg of sodium hydride (ca. 50% in mineral oil, ca. 1.3 eq.). Deprotonation was allowed to proceed at ambient temperature for 0.2 hours. The resultant solution of the corresponding sodium alkoxide was then treated at 0° with 0.112 ml of methyl iodide (2.6 eq.) and then kept for 2 hours at room temperature. Careful hydrolysis with cold water, extraction with EtOEt, washing with water and brine, drying over magnesium sulfate and evaporation of the solvent left a crude product, which was hydrolyzed as follows:

It was dissolved in 3 ml of THF and treated with 1.5 ml of 3N HCl. After 30 min. the mixture was poured onto crushed ice, extracted twice with AcOEt, washed with water and brine, dried over magnesium sulfate and evaporated to dryness. Purification of the residue by flash chromatography (silica gel with n-hexanetAcOEt=8/2) left finally 0.128 g of pure title compound as off-white gum, >98% pure according to gas chromatography.

EXAMPLE 17 a] 2-Cyclopropyl-8-ethoxy-8-methyl-2H-chromene-6-carbaldehyde 0.541 g of 3-ethoxy-4-hydroxy-5-iodo-benzaldehyde (1.85 mmol), 0.389 g of NaHCO$_3$ (4.63 mmol), 41.6 mg of Pd(OAc)2 (0.19 mmol) and 0.525 g of 2-cyclopropyl-but-3-en-2-ol (4.31 mmol) were mixed together under argon atmosphere in 3.7 ml of abs. DMF and heated for 3½ hours to 120°. The reaction mixture was cooled down to room temperature, poured onto crushed ice, extracted twice with AcOEt, washed with water and brine, dried over magnesium sulfate and evaporated to dryness. Flash chromatography (SiO$_2$ with n-hexane/AcOEt=82/18) yielded 298 mg of the title compound as light yellow oil.

MS: (MH)$^+$ 258, (M-CH$_3$)$^+$ 243.

b] 5-(2-Cyclopropyl-8-ethoxy-2-methyl-2H-chromen-6-ylmethyl)-pyrimidine-2,4-diamine To 298 mg of 2-cyclopropyl-8-ethoxy-2-methyl-2H-chromene-6-carbaldehyde (1.15 mmol), dissolved in 1.5 ml of abs. DMSO and 1.0 ml of t-butanol were added 185.5 mg of 3-anilinopropionitrile (1.1 eq.) and 155.3 mg of potassium t-butoxide (1.2 eq.), and the reaction was allowed to proceed for 2.5 hours at ambient temperature. Pouring onto crushed ice, twofold extraction with AcOEt, washing with water and brine, drying over magnesium sulfate and evaporation of the solvents left 497 mg of crude 2-(2-cyclopropyl-8-ethoxy-2-methyl-2H-chromen-6-ylmethyl)-3-phenylamino-acrylonitrile which was used as such.

The above prepared 497 mg of 2-(2-cyclopropyl-8-ethoxy-2-methyl-2H-chromen-6-ylmethyl)-3-phenylamino-acrylonitrile were treated with 361 mg of guanidine hydrochloride (3.3 eq.), 424 mg of potassium t-butoxide (3.3 eq.), and 23 ml of ethanol and kept in an oil bath of 90° for 6½ hours. The reaction mixture was then poured onto crushed ice, extracted twice with AcOEt, washed with water and brine, dried over magnesium sulfate and evaporated to dryness. Flash chromatography (SiO$_2$ with CH$_2$Cl$_2$MeOH/25% NH$_3$=19/1/0.05), followed by crystallization from EtOEt, delivered 175 mg of the title compound as pale-yellow crystals, mp. 195–196°.

ISP MS: (MH)$^+$ 353.3. NMR: (DMSO, 1H, δ, TMS) 0.25–0.4 (m,4H), 1.11 (m, 1H), 1.27 (t, J=7,3H), 1.35 (s, 3H), 3.45 (s, 2H), 3.98 (q, J=7, 2H), 5.52 (d, J=10, 1H), 5.66 (br s, 2H), 6.01 (br s, 2H), 6.35 (d, J=10, 1H), 6.46 (d, J=2, 1H), 6.72 (d, J=2, 1H), 7.47 (s, 1H).

EXAMPLE 18

5-(2-Cyclopropyl-8-mthoxy-2-methyl-2H-chromen-6-ylmethyl)-pyrimidine-2,4-diamine was pepared in analogy to example 17, but using in step a] the methoxy- instead of the ethoxy-derivative as starting material; light-yellow crystals, mp. 218–219°. ISP MS: (MH)$^+$ 339.3.

EXAMPLE 19

5-(8-Ethoxy-2,2-dimethyl-2H-chromen-6-ylmethyl)-pyrimidine-2,4-diamine was prepared in analogy to example 1, but using in step e] 8-ethoxy-2,2-dimethyl-2H-chromene-6-carbaldehyde (example 7a]) instead of 8-methoxy-2,2,4-trimethyl-2H-chromene-6-carbaldehyde; yellowish crystals of mp. 184–186°.

ISP MS: (MH)$^+$ 327.3. NMR: (DMSO, 1H, δ, TMS) 1.27 (t, J=7,3H), 1.34 (s, 3H), 3.46 (s, 2H), 3.98 (q, J=7, 2H), 5.66 (br s, 2H), 5.69 (d, J=9.5, 1H), 6.02 (br s) 2H), 6.30 (d, J=9.5, 1H) 6.48 (d, J=2, 1H), 6.74 (d, J=2, 1H), 7.48 (s, 1H).

EXAMPLE 20 a] 2',3',5',6'-Tetrahydro-8-methoxy-spiro[2H-1-benzopyran-2,4'-[4H]pyran]-6-carboxaldehyde 1.07 g of 5-iodo-vanilline (3.85 mmol), 0.808 g of NaHCO$_3$ (9.62 mmol), 86.4 mg of palladium diacetate (0.38 mmol), and 1.14 g of 4-vinyl-tetrahydro-pyran-4-ol (8.89 mmol) were mixed together under argon atmosphere in 9 ml of abs. DMS and heated for 3.5 hours to 120°. The reaction mixture was cooled down to room temperature, poured onto crushed ice, extracted twice with EtOEt, washed with water and brine) dried over magnesium sulfate and evaporated to dryness. Flash chromatography (SiO$_2$ with n-hexane/AcOEt=7/3) yielded 360 mg of the title compound as pale-yellow solid.

b] 5-[(2',3',5',6'-Tetrahydro-8-methocyspiro[2H-1-benzopyran-2,4'-[4H]pyran]-6-yl)-methyl]-2,4-pyrimidinediamine To 100 mg of 2',3',5',6'-tetrahydro-8-methoxy-spiro[2H-1-benzopyran-2,4'-[4H]pyran]-6-carboxaldehyde (0.485 mmol) dissolved in 1.5 ml of abs. DMSO and 1.0 ml of t-butanol were added 78 mg of 3-anilinopropionitrile (1.1 eq.) and 65 mg of potassium t-butoxide (1.2 eq.), and the reaction was allowed to proceed for 4.5 hours at ambient temperature. Pouring onto crushed ice, twofold extraction with AcOEt, washing with water, drying over sodium sulfate and evaporation of the solvents left 120 mg of crude intermediate which was used as such.

The above prepared 120 mg of crude condensation product was treated with 153 mg of guanidine hydrochloride (3.3 eq.), 180 mg of potassium t-butoxide (3.3 eq.), and 8 ml of ethanol and kept in an oil bath of 800 for 19 hours. The reaction mixture was then poured onto crushed ice, extracted twice with AcOEt, washed with water, dried over sodium sulfate and evaporated to dryness. Flash chromatography (SiO$_2$ with CH$_2$Cl$_2$/MeOH/25% NH$_3$=19//1/0.1), followed by crystalization from EtOEt, yielded 59 mg of the title compound as pale-yellow crystals.

ISP MS: (MH)$^+$ 355.3. NMR: (DMSO, 1H, δ, TMS) 1.65–1.8 (m, 4H), 3.48 (s, 2H), 3.63 (m, 2H), 3.73 (m, 2H), 3.75 (s, 3H), 5.67 (br s, 2H), 5.77 (d, J=10, 1H), 6.03 (br s, 2H), 6.40 (d, J=10, 1H), 6.50 (d, J=2, 1H), 6.80 (d, J=2, 1H), 7.49 (s, 1H).

EXAMPLE 21 a] 4-Bromo-2',3',5',6'-tetrahydro-8-methoxy-spiro[2H-1-benzopyran-2,4'-[4H]pyran]-6-carboxaldehyde 0.360 g of 2',3',5',6'-tetrahydro-8-methoxy-spiro[2H-1-benzopyran-2,4'-[4H]pyran]-6-carboxaldehyde (1.38 mmol) (example 20a) were dissolved in 3.6 ml of $CH_2Cl_2$ and cooled down to −78°. 6 ml of a 0.345M solution of bromine in methylene chloride (1.5 eq.) were added dropwise, and stirring continues for 90 min. Pouring onto crushed ice, twofold extraction with ether, washing with water and brine, drying over magnesium sulfate and evaporation of the solvents left 430 mg of the corresponding trans-dibromide as colourless solid which was used crude for the next step.

The above prepared trans-dibromide was dissolved in 10 ml of abs. THF and treated at 0° with 0.509 g of DBN (4 eq.). The reaction mixture was kept for 2 hours at room temperature and then quenched by pouring onto crushed ice. Extraction with EtOEt, washing with water and brine, drying over magnesium sulfate and evaporation of the solvents left a crude product which was purified by flash chromatography ($SiO_2$ with n-hexane/AcOEt=8/2) to yield 0.185 g of the title compound as white solid, mp. 107–108°.

MS: $(M)^+$ 338, 340, $(M—COH)^+$ 309, 311.

b] 5-[(4-Bromo-2',3',5',6'-tetrahydro-8-methoxyspiro[2H-1-benzopyran-2,4'-[4H]pyran]-6-yl)-methyl]-2,4-pyrimidinediamine To 121 mg of 4-bromo-2',3',5',6'-tetrahydro-8-methoxy-spiro[2H-1-benzopyran-2,4'-[4H]pyran]-6-carboxaldehyde (0.36 mmol) dissolved in 1.5 ml of abs. DMSO and 1.0 ml of butanol were added 54.8 mg of 3-anilinopropionitrile (1.5 eq.) and 44 mg of potassium t-butoxide (1.1 eq.), and the reaction was allowed to proceed for 3 hours at ambient temperature. Pouring onto crushed ice, twofold extraction with AcOEt, washing with water, drying over magnesium sulfate and evaporation of the solvents left 170 mg of crude product which was used as such.

The above prepared 170 mg were treated with 115 mg of guanidine hydrochloride (3.3 eq.), 147 mg of potassium t-butoxide (3.3 eq.), and 8 ml of ethanol and kept in an oil bath of 80° for 14 hours. The reaction mixture was then poured onto crushed ice, extracted twice with AcOEt, washed with water and brine, dried over magnesium sulfate and evaporated to dryness. Flash chromatography ($SiO_2$ with $CH_2Cl_2$/MeOH/25% $NH_3$=19/1/0.05) yielded 46 mg of the title compound as pale-yellow crystals, mp. 232–233°.

ISP MS: $(MH)^+$ 433.4, 435.4. NMR: (DMSO, 1H, δ, TMS) 1.7–1.8 (m,4H),3.55 (s,2H),3.6–3.75 (m,4H),3.77 (s, 3H), 5.68 (br s, 2H), 6.09 (br s, 2H), 6.33 (s, 1H), 6.80 (d, J=2, 1H), 6.95 (d, J=2, 1H), 7.52 (s, 1H).

EXAMPLE 22

4-Bromo-6-[(2,4-diamino-5-pyrimidinyl)methyl]-8-methoxy-spiro[2H]-1-benzopyran-2,4'-piperidine-1'-carboxylic acid 1,1-dimethylethyl ester was prepared in analogy to example 21, but using in step a] 6-formyl-8-methoxy-spiro[2H-1-benzopyran-2,4'-piperidine]-1'-carboxylic acid 1,1-dimethylethyl ester instead of 2',3',5',6'-tetrahydro-methoxy-spiro[2H-1-benzopyran-2,4'-[4H]pyran]-6-carboxaldehyde as starting material; light-yellow crystals, mp. 2360. The starting compound was prepared as described in example 20, but using in step a] 4-hydroxy-4-vinyl-piperidine-1-carboxylic acid 1,1-dimethyl-ethyl ester instead of 4-vinyl-tetrahydro-pyran-4-ol.

ISP MS: $(MH)^+$ 532.3, 534.3. NMR: (DMSO, 1H, δ, TMS) 1.40 (s, 9H), 1.6–1.7 (m, 2H), 1.8–1.85 (m, 2H), 3.16 (br s, 2H), 3.55 (s, 2H), 3.70 (m, 2H), 3.76 (s, 3H), 5.69 (br s,2H), 6.10 (br s, 2H), 6.29 (s, 1H), 6.80 (d, J=2, 1H), 6.95 (d, J=2, 11H), 7.52 (s, 1H).

EXAMPLE 23

4-Bromo-6-[(2,4-diamino-5-pyrimidinyl)methyl]-8-ethoxy-spiro [2H]-1-benzopyran-2,4'-piperidine-1'-carboxylic acid 1,1-dimethylethyl ester was prepared in analogy to example 22, but starting the whole reaction sequence with 3-ethoxy-4-hydroxy-5-iodo-benzaldehyde instead of 5-iodo-vanilline; orange crystals, mp. 235–236° (dec.).

ISP MS: $(MH)^+$ 546.1, 548.1. NMR: (DMSO, 1H, δ, TMS) 1.30 (t, J=7, 3H), 1.40 (s, 9H), 1.6–1.7 (m, 2H), 1.75–1.85 (m, 2H), 3.05–3.25 (m, 2H), 3.54 (s, 2Hi), 3.72 (m, 2H), 4.01 (q, J=7, 2H), 5.68 (br s, 2H), 6.09 (br s, 2H), 6.28 (s, 1H), 6.80 (s, 1H), 6.92 (s, 1H), 7.52 (s, 1H).

EXAMPLE 24

5-[(4-Bromo-8-methoxyspiro[2H-1-benzopyran-2,4'-piperidin]-6-yl)methyl]-2,4-pyrimidinediamine 155 mg of 4-bromo-6-[(2,4-diamino-5-pyrimidinyl)methyl]-8-methoxy-spiro[2H]-1-benzopyran-2,4'-piperidine-1'-carboxylic acid 1,1-dimethylethyl ester (0.29 mmol, example 22) was dissolved in 3 ml of abs. methylene chloride, treated with 0.60 ml of trifluoroacetic acid, and the reaction was allowed to proceed for 1.5 hours at ambient temperature. Evaporation of the solvents, followed by flash chromatography ($SiO_2$ with $CH_2Cl_2$/MeOH/25% $NH_3$=90/10/1) yielded 125 mg of the title compound as pale-yellow crystals, mp. >2700.

ISP MS: $(MH)^+$ 432.4, 434.4. NMR: (DMSO, 1H, δ, TMS) 1.6–1.7 (m, 2H), 1.75–1.8 (m, 2H), 2.7–2.8 (m, 2H), 2.8–2.9 (m, H), 3.55 (s, 2H), 3.76 (s, 3H), 5.68 (br s, 2H), 6.08 (br s, 2H), 6.30 (s, 1H), 6.79 (d, J=2, 1H), 6.93 (d, J=2, 1H), 7.52 (s, 1H).

EXAMPLE 25

6-[(2,4-Diamino-5-pyrimidinyl)methyl]-8-ethoxy-4-(3-hydroxy-1-butynyl)spiro[2H]-1-benzopyran-2,4'-piperidine-1'-carboxylic acid 1,1-dimethylethyl ester was prepared in analogy to examples 15 and 22 as light-yellow solid, mp.141–143°.

ISP MS: $(MH^+$ 536.3. IR $(cm^{-1})$: 3469, 3355, 2925, 2854, 1688, 1623, 1565, 1461, 1424, 1366, 1262, 1244, 1157, 1110, 1066, 1032, 972, 868.

EXAMPLE 26

6-[(2,4-Diamino-5-pyrimidinyl)methyl]-8-methoxy-spiro [2H]-1-benzopyran-2,4'-piperidine-1'-carboxylic acid 1,1-dimethylethyl ester was prepared in analogy to example 22, but omitting the bromination/dehydro-bromination-sequence; pale-yellow crystals, mp. 192–193°.

ISP MS: $(MH)^+$ 454.5.

EXAMPLE 27

5-[(8-methoxyspiro[2H-1-benzopyran-2,4'-piperidine]-6-yl)methyl]-2,4-pyrimidine-diamine was prepared in analogy to example 24, but using the product of example 26 as starting material; yellow crystals.

ISP MS: $(MH)^+$ 354.4.

EXAMPLE 28

6-[(2,4-Diamino-5-pyrimidinyl)methyl]-ethoxy-spiro[2H]-1-benzopyran-2,4'-piperidine-1'-carboxylic acid 1,1-dimethylethyl ester was prepared in analogy to example 26, but using the ethoxy- instead of the methoxy-intermediate; yellow crystals, mp. 209–212° (dec.).

ISP MS: $(MH)^+$ 468.3.

EXAMPLE 29 a] 8-Methoxy-spiro[2H-1-benzopyran-2,1'-cyclobutane]-6-carboxaldehyde 1.444 g of 5-iodo-vanilline (5.19 mmol), 1.745 g of NaHCO$_3$ (20.8 mmol), 117 mg of palladium diacetate (0.52 mmol) and 1.019 g of 1-vinyl-cyclobutanol (10.4 mmol) were mixed together in an argon atmosphere in 14 ml of abs. DMF and heated for 3.5 hours to 120°. The reaction mixture was cooled to room temperature, poured onto crushed ice, extracted twice with EtOEt, washed with water and brine, dried over magnesium sulfate and evaporated to dryness. Flash chromatography (SiO$_2$ with n-hexane/AcOEt=8/2) yielded 0.137 g of the title compound as pale-yellow oil.

b] 4-Bromo-8-methoxy-spiro[2H-1-benzopyran-2,1'-cyclobutane]-6-carboxaldehyde was prepared from the product of example 29a] as described in example 1b]; off-white crystals, mp. 128–129°.

MS: (M)$^+$ 308.1, 310.1 (M—CO)$^+$ 280.0, 282.0. NMR: (DMSO, 1H, δ, TMS) 1.7–1.9 (m, 2H), 2.25–2.35 (m, 2H), 2.35–2.45 (m, 2H), 3.88 (s, 3H), 6.83 (s, 1H), 7.49 (d, J=1, 1H), 7.53 (d, J=2, 1H), 9.87 (s, 1H).

c] 5-[(4-Bromo-8-methoxyspiro[2H-1-benzopyran-2,1'-cyclobutan]-6-yl)methyl]-2,4-pyrimidinediamine To 94 mg of 4-bromo-8-methoxy-spiro[2H-1-benzopyran-2,1'-cyclobutane]-6-carboxaldehyde (0.30 mmol) dissolved in 1.2 ml of abs. DMSO and 0.8 ml of t-butanol were added 46.7 mg of 3-anilinopropionitrile (1.05 eq.) and 37.5 mg of potassium t-butoxide (1.1 eq.), and the reaction was allowed to proceed for 2.5 hours at ambient temperature. Pouring onto crushed ice, twofold extraction with AcOEt, washing with water and brine, drying over magnesium sulfate and evaporation of the solvents left 133 mg of crude product which was used as such.

The above prepared 133 mg of crude condensation product was treated with 95.8 mg of guanidine hydrochloride (3.3 eq.), 112.6 mg of potassium t-butoxide (3.3 eq.), and 4.5 ml of ethanol and kept in an oil bath of 80° for 6 hours. The reaction mixture was then poured onto crushed ice, extracted twice with AcOEt, washed with brine, dried over magnesium sulfate and evaporated to dryness. Flash chromatography (SiO$_2$ with CH$_2$Cl$_2$/MeOH/25% NH$_3$=19/1/0.05) followed by crystallization from EtOEt yielded 54 mg of the title compound as pale-yellow crystals, mp.231–232°.

ISP MS: (MH)$^+$ 403.3, 405.3. NMR: (DMSO, 1H, δ, TMS) 1.7–1.85 (m, 2H), 2.18–2.25 (m, 2H), 2.27–2.38 (m, 2H), 3.54 (s, 2H), 3.76 (s, 3H), 5.68 (br s, 2H), 6.08 (br s, 2H), 6.65 (s, 1H), 6.77 (d, J=2, 1H), 6.91 (d, J=2, 1H), 7.52 (s, 1H).

EXAMPLE 30

5-[(4-Bromo-8-ethoxyspiro[2H-1-benzopyran-2,1'-cyclobutan]-6-yl)methyl]-2,4-pyrimidinediamine was prepared in analogy to example 29, but using the ethoxy- instead of the methoxy-intermediate; yellow crystals, mp. 213–214°.

ISP MS: (MH)$^+$ 417.2, 419.2.

EXAMPLE 31

5-[(8-Methoxyspiro[2H-1-benzopyran-2,1'-cyclohexan]-6-yl)methyl]-2,4-pyrimidine-diamine as prepared in analogy to example 17, but starting with 5-iodo-vanilline and 1-vinyl-cyclohexanol; yellow crystals, mp. 181–182°.

ISP MS: (MH)$^+$ 353.3.

EXAMPLE 32 a] 4-(4-Fluoro-phenyl)-8-methoxy-2,2-dimethyl-2H-chromene-6-carbaldehyde 235 mg of 4-bromo-6-[1,3]dioxolan-2-yl-8-methoxy-2,2-dimethyl-2H-chromene (0.689 mmol) (example 1c), 145 mg of 4-fluorophenyl boronic acid (1.5 eq.), and 39.8 mg of tetrakis-triphenylphosphine-palladium (0.05 eq.) were mixed together in an argon atmosphere in 3 ml of abs. DMF and 1.5 ml of 2M K$_3$PO$_4$ and heated for 2 hours to 80°. The reaction mixture was cooled to room temperature, poured onto crushed ice/conc. HCl/AcOEt and vigorously stirred to cleave the acetal. Separation of the layers, washing the aqueous phase with water, drying over sodium sulfate and evaporation of the solvents yielded 500 mg crude product. Flash chromatography (SiO$_2$ with n-hexane/AcOEt=8/2) gave 199 mg of the title compound as colourless gum.

MS: (M)$^+$ 312.1, (M-CH$_3$)$^+$ 297.1.

b] 5-[4-(4-Fluoro-phenyl)-8-methoxy-2,2-dimethyl-2H-chromen-6-ylmethyl]-pyrimidine-2,4-diamine To 194 mg of 4-(4-fluoro-phenyl)-8-methoxy-2,2-dimethyl-2H-chromene-6-carbaldehyde (0.621 mmol) dissolved in 2 ml of abs. DMSO and 1.3 ml of t-butanol were added 100 mg of 3-anilinopropionitrile (1.1 eq.) and 84 mg of potassium t-butoxide (1.2 eq.), and the reaction was allowed to proceed for 4 hours at ambient temperature. Pouring onto crushed ice, twofold extraction with AcOEt, washing with water, drying over sodium sulfate and evaporation of the solvents left crude 2-[4-(4-fluoro-phenyl)-8-methoxy-2,2-dimethyl-2H-chromen-6-ylmethyl]-3-phenylamino-acrylonitrile which was used as such.

The above prepared crude 2-[4-(4-fluoro-phenyl)-8-methoxy-2,2-dimethyl-2H-chromen-6-ylmethyl]-3-phenylaminoacrylonitrile was treated with 196 mg of guanidine hydrochloride (3.3 eq.), 230 mg of potassium t-butoxide (3.3 eq.) and 14 ml of ethanol and kept in an oil bath of 80° for 14 hours. The reaction mixture was then poured onto crushed ice, extracted twice with AcOEt, washed with water, dried over sodium sulfate and evaporated to dryness. Flash chromatography (SiO$_2$ with CH$_2$Cl$_2$/MeOH/25% NH$_3$=19/1/0.05) followed by crystallization from EtOEt/n-hexane yielded 21 mg of the title compound as pale-yellow crystals, mp. 265° dec.

ISP MS: (MH)$^+$ 407.4. NMR: (DMSO, 1H, δ, TMS) 1.40 (s, 6H), 3.45 (s, 2H), 3.74 (s, 3H), 5.66 (br s,2H), 5.73 (s, 1H),6.03 (br s, 2H),6.42 (d, J=2, 1H),6.81 (d, J=2,1H),7.22 (t, J=9, 2H),7.32 (m,2H), 7.40 (s, 1H).

EXAMPLE 33

5-[4-(3-Fluoro-phenyl)-8-methoxy-2,2-dimethyl-2H-chromen-6-ylmethyl]-pyrimidine-2,4-diamine was prepared in analogy to example 32 but using 3-fluorophenyl boronic acid instead of the 4-F-derivative; pale-yellow crystals, mp. 267° dec.

MS: (M)$^+$ 406.1, (M-CH$_3$)$^+$ 391.1.

EXAMPLE 34

5-[8-Ethoxy-4-(3-fluoro-phenyl)-2,2-dimethyl-2H-chromen-6-ylmethyl]-pyrimidine-2,4-diamine was prepared in analogy to example 33 but using the ethoxy- instead of the methoxy-intermediate; yellow crystals, mp. 185–186°.

ISP MS: (MH)$^+$ 421.4.

EXAMPLE 35

5-[8-Ethoxy-4-(4-fluoro-phenyl)-2,2-dimethyl-2H-chromen-6-ylmethyl]-pyrimidine-2,4-diamine was prepared in analogy to example 34 but using 4-fluorophenyl boronic acid instead of the 3-F-derivative; pale-yellow crystals, mp. 204–205° dec.

MS: (M)$^+$ 420.2, (M-CH$_3$)$^+$ 405.2. IR (cm$^{-1}$): 3454, 3433, 2976, 1642, 1624, 1556, 1453, 1433, 1355, 1264, 1217, 1141, 1071, 958, 819, 792.

EXAMPLE 36

5-(8-Ethoxy-2,2-dimethyl-4-thiophen-2-yl-2H-chromen-6-ylmethyl)-pyrimidine-2,4-diamine was prepared in analogy to example 35 but using 2-thiophene boronic acid instead of 4-fluorophenyl boronic acid; yellow crystals, mp. 213–214° dec.

MS: $(M)^+$ 408.2, $(M-CH_3^+$ 393.1. NMR: (DMSO, 1H, δ, TMS) 1.30 (t, J=7, 3H), 1.39 (s, 6H), 3.49 (s, 2H), 4.02 (q, J=7, 2H), 5.65 (br s, 2H), 5.90 (s, 1H), 6.04 (br s, 2H), 6.81 (d, J=2, 1H), 6.83 (d, J=2, 1H), 7.10 (m, 2H), 7.45 (s, 1H), 7.53 (m, 1H).

EXAMPLE 37

5-(8-Ethoxy-2,2-dimethyl-4-thiophen-3-yl-2H-chromen-6-ylmethyl)-pyrimidine-2,4-diamine was prepared in analogy to example 36 but using 3-thiophene boronic acid instead of the 2-substituted analogue; yellow crystals, mp. 217° dec.

MS: $(M)^+$ 408.2, $(M-CH_3)^+$ 393.2. IR $(cm^{-1})$: 3455, 3431, 2923, 2853, 1648, 1630, 1557, 1466, 1264, 1217, 1139, 1072, 937, 840, 792.

EXAMPLE 38 a] 4-(8-Ethoxy-6-formyl-2,2-dimethyl-2H-chromen-4-yl)-benzonitrile 250 mg of 4-bromo-6-[1,3]dioxolan-2-yl-8-ethoxy-2,2-dimethyl-2H-chromene (0.700 mmol), 241 mg of 4-cyanophenyl boronic acid (1.5 eq.), and 40.7 mg of tetrakis-triphenylphosphine-palladium (0.05 eq.) were mixed together in an argon atmosphere in 3.2 ml abs. DMF and 1.6 ml of 2M $K_3PO_4$ and heated for 1.5 hours to 800. The reaction mixture was cooled to room temperature, poured onto crushed ice/conc. HCl/EtOEt and vigorously stirred to cleave the acetal. Separation of the layers, washing the organic phase with water, drying over sodium sulfate and evaporation of the solvents, followed by flash chromatography ($SiO_2$ with n-hexane/AcOEt=8/2) yielded 244 mg of the title compound as off-white foam.

MS: $(M)^+$ 333.2, $(M-CH_3)^+$ 318.2.

b] 4-[6-(2,4-Diamino-pyrimidin-5-ylmethyl)-8-ethoxy-2,2-dimethyl-2H-chromen-4-yl]-benzonitrile To 235 mg of 4-(8-ethoxy-6-formyl-2,2-dimethyl-2H-chromen-4-yl)-benzonitrile (0.700 mmol) dissolved in 0.94 ml of abs. DMSO and 0.56 ml of t-butanol were added 113.2 mg of 3-anilinopropionitrile (1.1 eq.) and 94.8 mg of potassium t-butoxide (1.2 eq.), and the reaction was allowed to proceed for 2.5 hours at ambient temperature. Pouring onto crushed ice, twofold extraction with AcOEt, washing with brine, drying over sodium sulfate and evaporation of the solvents left 325 mg of crude 4-[6-(2-cyano-3-phenylamino-allyl)-8-ethoxy-2,2-dimethyl-2H-chromen-4-yl]-benzonitrile, which was used as such.

The above prepared crude 4-[6-(2-cyano-3-phenylamino-allyl)-8-ethoxy-2,2-dimethyl-2H-chromen-4-yl]-benzonitrile was treated with 222 mg of guanidine hydrochloride (3.3 eq.), 261 mg of potassium t-butoxide (3.3 eq.), and 13 ml of ethanol and kept in an oil bath of 80° for 15 hours. The reaction mixture was then poured onto crushed ice, extracted twice with AcOEt, washed with brine, dried over sodium sulfate and evaporated to dryness. Flash chromatography ($SiO_2$ with $CH_2Cl_2$/MeOH/25% $NH_3$=19/1/0.05) followed by crystallization from EtOEt yielded 110 mg of the title compound as yellow crystals, mp. 219–220° dec.

ISP MS: $(MH)^+$ 428.5. NMR: (DMSO, 1H, δ, TMS) 1.30 (t, J=7,3H), 1.41 (s, 6H), 3.43 (s, 2H), 4.02 (q, J=7, 2H), 5.65 (br s, 2H), 5.88 (s, 1H), 6.03 (br s, 2H), 6.42 (d, J=2, 1H), 6.80 (d, J=2, 1H), 7.42 (s, 1H), 7.48 (d, J=8, 2H), 7.86 (d, J=8, 1H).

EXAMPLE 39

5-[(4-(4-Cyano-phenyl)-8-methoxyspiro[2H-1-benzopyran-2,1'-cyclobutan]-6-yl)methyl]-2,4-pyrimidinediamine was prepared in analogy to example 38, but using in step a] 4-bromo-8-methoxy-spiro[2H-1-benzopyran-2,1'-cyclobutane]-6-carboxaldehyde (prepared in example 29b) instead of 4-bromo-6-[1,3]dioxolan-2-yl-8-ethoxy-2,2-dimethyl-2H-chromene as coupling partner; yellow crystals, mp. 214–215° dec.

ISP MS: $(MH)^+$ 426.4, $(M-C_2H_{4T})^+$ 398.3. NMR: (DMSO, 1H, δ, TMS) 1.7–1.85 (m, 2H), 2.19–2.28 (m, 2H), 2.30–2.40 (m, 2H), 3.44 (s, 2H), 3.77 (s, 3H), 5.65 (br s, 2H), 6.04 (br s, 2H), 6.28 (s, 1H), 6.41 (d, J=2, 1H), 6.83 (d, J=2, 1H), 7.43 (s, 1H), 7.53 (d, J=8.5, 2H), 7.88 (d, J=8.5, 2H).

EXAMPLE 40 a] 8-Ethoxy-6-formyl-spiro[2H-1-benzopyran-2,4'-piperidine]-1'-carboxylic acid 1,1-dimethylethyl ester 0.514 g of 3-ethoxy-4-hydroxy-5-iodo-benzaldehyde (1.76 mmol), 0.537 g of $NaHCO_3$ (4.40 mmol), 39.5 mg of palladium diacetate (0.18 mmol), and 0.500 g of 4-hydroxy-4-vinyl-piperidine-1-carboxylic acid 1,1-dimethyl-ethyl ester (2.20 mmol) were mixed together under argon atmosphere in 4.8 ml of abs. DMF and heated for 5.5 hours to 120°. The reaction mixture was cooled down to room temperature, poured onto crushed ice, extracted twice with AcOEt, washed with brine, dried over magnesium sulfate and evaporated to dryness. Flash chromatography ($SiO_2$ with n-hexane/AcOEt=8/2) yielded 189 mg of the title compound as pale-yellow oil.

ISP MS: $(MNa)^+$ 396.3, $(MH)^+$ 374.4.

b] 4-Bromo-8-ethoxy-6-formyl-spiro[2H-1-benzopyran-2,4'-piperidine]-1'-carboxylic acid 1,1-dimethylethyl ester was prepared from the product of example 40 a] as described in example 1 b]; off-white crystals, mp. 148–150°.

ISP MS: $(MNa)^+$ 474.2, 476.2, $(MH)^+$ 452.4, 454.4.

c] 4-Bromo-6-(1,3-dioxolan-2-yl)-8-ethoxy-spiro[2H-1-benzopyran-2,4'-piperidine]-1'-carboxylic acid 1,1-dimethylethyl ester was prepared from the above compound of example 40 b] as described in example 1 c]; white foam.

ISP MS: $(MNa)^+$ 518.1, 520.1, $(MH)^+$ 496.1, 498.1.

d] 4-(4-Cyanophenyl)-8-ethoxy-6-formyl-spiro[2H-1-benzopyran-2,4'-piperidine]-1'-carboxylic acid 1,1-dimethylethyl ester 250 mg of 4-bromo-6-(1,3-dioxolan-2-yl)-8-ethoxy-spiro[2H-1-benzopyran-2,4'-piperidine]-1'-carboxylic acid 1,1-dimethylethyl ester (0.500 mmol), 150 mg of 4-(4,4,5,5-tetramethyl[1,3,2]dioxaborolan-2-yl)-benzonitrile (1.3 eq.), and 29.1 mg of tetrakis-(triphenylphosphine)-palladium (0.05 eq.) were mixed together under argon atmosphere in 2.3 ml of abs. DMF and 1.15 ml of 2M $K_3PO_4$ and heated for 2 hours to 80°. The reaction mixture was cooled to room temperature, poured onto crushed ice/conc. HCl/AcOEt, and vigorously stirred for 2 hours to cleave the acetal. Separation of the layers, washing the organic phase with brine, drying over sodium sulfate and evaporation of the solvents, followed by flash chromatography ($SiO_2$ with n-hexane/AcOEt=8/2) afforded 214 mg of the title compound as off-white solid.

ISP MS: $(MNa)^+$ 497.2, $(MH)^+$ 475.3.

c] 4-(4-Cyanophenyl)-6-[(2,4-diamino-5-pyrimidinyl)methyl]-8-ethoxy-spiro[2H-1-benzopyran-2,4'-piperidine]-1'-carboxylic acid 1,1-dimethylethyl ester To 210 mg of 4-(4-cyanophenyl)-8-ethoxy-6-formyl-spiro[2H-1-benzopyran-2,4'-piperidine]-1'-carboxylic acid 1,1-dimethylethyl ester (0.44 mmol) dissolved in 0.59 ml of abs. DMSO and 0.35 ml of t-butanol were added 71.2 mg of 3-anilinopropionitrile (1.1 eq.) and 59.6 mg of potassium t-butoxide (1.2 eq.), and the reaction was allowed to proceed for 3.75 hours at ambient temperature. Pouring onto crushed ice, twofold extraction with AcOEt, washing with brine, drying over sodium sulfate and evaporation of the solvents left 325 mg of crude product which was used as such.

The above prepared crude condensation product was treated with 144 mg of guanidine hydrochloride (3.3 eq.), 164 mg of potassium t-butoxide (3.3 eq.), and 8 ml of ethanol and kept in an oil bath of 80° for 14 hours. The reaction mixture was then poured onto crushed ice, extracted twice with AcOEt, washed with brine, dried over sodium sulfate and evaporated to dryness. Flash chromatography ($SiO_2$ with $CH_2Cl_2$/MeOH/25% $NH_3$=19/1/0.05) followed by crystallization from EtOEt, yielded 48 mg of the title compound as yellow crystals, mp. 241–243° dec.

ISP MS: (MH)$^+$ 569.2. NMR: (DMSO, 1H, δ, TMS) 1.31 (t, 3H), 1.41 (s, 9H), 1.6–1.7 (m,2H), 1.78–1.9 (m, 2H), 3.15–3.3 (m, 2H), 3.44 (s, 2H), 3.72 (m, 2H), 4.02 (m),2H), 5.65 (br s, 2H), 5.93 (s, 1H), 6.05 (br s, 2H), 6.44 (s, 1H), 6.84 (s, 1H), 7.44 (s, 1H), 7.51 (d, J=7, 2H), 7.86 (d, J=7, 2H).

EXAMPLE 41

5-(8-Cyclopropylmethoxy-2,2-dimethoxy-2H-chromen-6-ylmethyl)-pyrimidine-2,4-diamine was prepared in analogy to example 1, but using in step e] 8-cyclopropylmethoxy-2,2-dimethyl-2H-chromene-6-carbaldehyde as coupling partner; pale-yellow crystals, mp. 204–206°.

ISP MS: (MH)$^+$ 353.3. NMR: ($CDCl_3$, 1H, δ, TMS) 0.32 (m),2H), 0.57 (m, 2H), 1.25 (m, 1H), 1.45 (s, 6H), 3.58 (s, 2H), 3.81 (d, J=7, 2H), 4.50 (br s, 2h), 4.62 (br s, 2H), 5.61 (d, J=10, 1H), 6.23 (d, J=10, 1H), 6.46 (d, J=2, 1H), 6.62 (d, J=2, 1H), 7.78 (s, 1H).

EXAMPLE 42

5-(8-Methoxy-2,2-dimethyl-4-phenyl-2H-chromen-6-ylmethyl)-pyrimidine-2,4-diamine was prepared in analogy to example 32, but using in step a] phenylboronic acid; yellow crystals, mp. >260°.

MS: (M)$^+$ 388, (M-$CH_3$)$^+$ 373.

EXAMPLE 43

2-[6-(2,4-Diamino-pyrimidin-5-ylmethyl)-8-ethoxy-2,2-dimethyl-2H-chromen-4-yl]-propan-2-ol was obtained as yellow crystals, mp. 209–210°.

ISP MS: (MH)$^+$ 385.4. NMR: (DMSO, 1H, δ, TMS) 1.26 (t, J=7, 3H), 1.31 (s,6H), 1.36 (s, 6H), 3.48 (s, 2H), 3.96 (q, J=7, 2H), 4.82 (s, 1H), 5.63 (br s, 2H), 5.71 (s, 1H), 6.03 (br s, 2H), 6.72 (d, J=2, 1H), 7.36 (d, J=2, 1H), 7.43 (s, 1H). This product was prepared in analogy to example 8, but using acetone instead of methyl iodide as electrophile yielding 8-ethoxy-4-(1-hydroxy-1-methyl-ethyl)-2,2-dimethyl-2H-chromene-6-carbaldehyde according to the following experimental procedure:

8-Ethoxy-4-(1-hydroxy-1-methyl-ethyl)-2,2-dimethyl-2H-chromene-6-carbaldehyde 385 mg of 4-bromo-6-[1,3] dioxolan-2-yl-8-ethoxy-2,2-dimethyl-2H-chromene (1.08 mmol) were dissolved in 9 ml of abs. THF and treated at −78° with 0.867 ml of n-butyl lithium (1.5M, n-hexane, 1.2 eq.). 15 min. later 0.239 ml of acetone (3 eq.) dissolved in 2 ml of abs. THF were added and the cooling bath removed after 10 min. After additional 20 min. the reaction mixture was poured onto crushed ice/ AcOEt, the organic layer washed with water and brine, dried over magnesium sulfate and evaporated to dryness. The crude product was hydrolyzed as follows:
The above prepared 2-(6-[1,3]dioxolan-2-yl-8-ethoxy-2,2-dimethyl-2H-chromen-4-yl)-propan-2-ol was dissolved in 6 ml of methanol and 3 ml of water and treated with 54 mg of pyridinium p-toluenesulfonate. After 15 min. at room temperature, the reaction mixture was poured onto crushed ice/AcOEt, the organic layer washed with water, dried over magnesium sulfate and evaporated to dryness. Flash chromatography ($SiO_2$ with n-hexane/AcOEt=7/3) yielded 194 mg of the title compound as colourless oil.

MS: (M)$^+$ 290, (M-$CH_3$)$^+$ 275.

EXAMPLE 44

2-[6-(2,4-Diamino-pyrimidin-5-ylmethyl)-8-ethoxy-2,2-dimethyl-2H-chromen-4-yl]-butan-2-ol was prepared in analogy to example 43 but using 2-butanone as electrophile instead of acetone; beige crystals, mp. 127–128°.

ISP MS: (MH)$^+$ 399.5.

EXAMPLE 45

5-(8-Ethoxy-4-isopropenyl-2,2-dimethyl-2H-chromen-6-ylmethyl)-pyrimidine-2,4-diamine was obtained as yellowish crystals, mp. 188–189°.

ISP MS: (MH)$^+$ 367.2. NMR: (DMSO, 1H, δ, TMS) 1.28 (t) J=7, 3H), 1.33 (s, 6H), 1.86 (s, 3H), 3.49 (s, 2H), 4.00 (q, J=7, 2H), 4.95 (br s, 1H), 5.11 (br s, 1H), 5.61 (s, 1H), 5.66 (br s, 2H), 6.04 (br s, 2H), 6.58 (d, J=2, 1H), 6.77 (d, J=2, 1H), 7.47 (s, 1H).

The product was prepared in analogy to example 43 but treating, before elaborating the diaminopyrimidine ring, the intermediate 8-ethoxy-4-(1-hydroxy-1-methyl-ethyl)-2,2-dimethyl-2H-chromene-6-carbaldehyde with 1 eq. of p-toluene sulfonic acid in methylene chloride at 35° for 14 hours to give the necessary 8-ethoxy-4-isopropenyl-2,2-dimethyl-2H-chromene-6-carbaldehyde.

EXAMPLE 46

3-[6-(2,4-Diamino-pyrimidin-5-ylmethyl)-8-methoxy-2,2-dimethyl-2H-chromen-4-yl]-prop-2-yn-1-ol was prepared in analogy to example 14 but using the methoxy-derivative as starting material; yellowish crystals, mp. 236–237°.

ISP MS: (MH)$^+$ 367.2.

EXAMPLE 47

5-(8-Ethoxy-2,2-dimethyl-4-pyridin-4-yl-2H-chromen-6-ylmethyl)-pyrimidine-2,4-diamine was prepared in analogy to example 38 but using 4-pyridine boronic acid in step a]; yellow crystals, mp. 223–226°.

ISP MS: (MH)$^+$ 404.5. IR (cm$^{-1}$): 3494, 3382, 2924, 2854, 1646, 1617, 1590, 1550, 1450, 1374, 1293, 1151, 1068, 936, 896, 852, 817, 793.

EXAMPLE 48

5-[4-(3,4-Dimethoxy-phenyl)-8-ethoxy-2,2-dimethyl-2H-chromen-6-ylmethyl]-pyrimidine-2,4-diamine was prepared in analogy to example 38 but using 3,4-dimethoxyphenyl boronic acid; beige crystals, mp. 191–192°.

MS: (M)$^+$ 462, (M-$CH_3$)$^+$ 447.

EXAMPLE 49

N-{3-[6-(2,4-Diamino-pyrimidin-5-ylmethyl)-8-ethoxy-2,2-dimethyl-2H-chromen-4-yl]-phenyl}-acetamide was prepared in analogy to example 47 but using 3-acetamidophenyl boronic acid; yellow crystals, mp. 145° dec.

ISP MS: (MH)$^+$ 460.5.

EXAMPLE 50
5-(8-Ethoxy-2,2-dimethyl-4-pyridin-3-yl-2H-chromen-6-ylmethyl)-pyrimidine-2,4-diamine was prepared in analogy to example 38 but using in step a] pyridine-3-boronic acid 1,3-propanediol cyclic ester; yellow crystals, mp. 145° dec.
ISP MS: (MH)$^+$ 404.5.

EXAMPLE 51
5-(8-Methoxy-2,2-dimethyl-4-thiophen-2-yl-2H-chromen-6-ylmethyl)-pyrimidine-2,4-diamine was prepared in analogy to example 36 but using the 8-methoxy- instead of the 8-ethoxy-derivative; yellow crystals, mp. >260°.
MS: (M)$^+$ 394, (M-CH$_3$ 379.

EXAMPLE 52
5-[8-Ethoxy-4-(4-ethoxy-phenyl)-2,2-dimethyl-2H-chromen-6-ylmethyl]-pyrimidine-2,4-diamine was prepared in analogy to example 38 but using in step a] 4-ethoxyphenyl boronic acid; pale yellow crystals, mp. 186–188°.
ISP MS: (MH)$^+$ 447.4.

EXAMPLE 53
5-[8-Methoxy-2,2-dimethyl-4-(3-nitro-phenyl)-2H-chromen-6-ylmethyl]-pyrimidine-2,4-diamine was prepared in analogy to example 38 but using in step a]3-nitrophenyl boronic acid and starting with the methoxy derivative; yellow crystals, mp. 253–254°.
ISP MS: (MH)$^+$ 434.5.

EXAMPLE 54
a] [4-(6-Formyl-8-methoxy-2,2-dimethyl-2H-chromen-4-yl)-phenyl]-carbamic acid t-butyl ester
459 mg of (4-bromo-phenyl)-carbamic acid t-butyl ester (1.69 mmol), 536 mg of 4,4,5,5,4',4',5',5'-octamethyl-[2,2']bi[[1,3,2]dioxaborolanyl] (2.11 mmol), 553 mg of potassium acetate (5.63 mmol), and 84.7 mg of Pd(dppf)Cl$_2$ (0.12 mmol) were mixed together under argon atmosphere in 11 ml of abs. DMF and heated for 18 hours to 80°. 394 mg of 4-bromo-6-[1,3]dioxolan-2-yl-8-methoxy-2,2-dimethyl-2H-chromene (1.15 mmol), 133 mg of tetrakis-(triphenylphosphine)-palladium (0.12 mmol), and 2.1 ml of 2M potassium phosphate were added and heating continued for 18 hours at 80°. The reaction mixture was cooled to room temperature, poured onto crushed ice/AcOEt, the organic layer washed with water and brine, dried over magnesium sulfate and evaporated to dryness to afford 523 mg of crude acetal which was cleaved as follows:
The above prepared intermediate was dissolved in 6.4 ml of methanol, 3.2 ml of water, and 4.0 ml of THF and treated with 116 mg of pyridinium p-toluene sulfonate (0.4 eq.). After 120 min. at room temperature the reaction mixture was poured onto crushed ice/AcOEt, the organic layer washed with water and brine, dried over magnesium sulfate and evaporated to dryness. Flash chromatography (SiO$_2$ with n-hexane/AcOEt=65/35) produced 357 mg of the title compound as colourless oil.
ISP MS: (MNa)$^+$ 432.4, (MNH$_4$) 427.5, (MH)$^+$ 410.4.
b] {4-[6-(2,4-Diamino-pyrimidin-5-ylmethyl)-8-methoxy-2,2-dimethyl-2H-chromen-4-yl]-phenyl}-carbamic acid t-butyl ester
To 353 mg of [4-(6-formyl-8-methoxy-2,2-dimethyl-2H-chromen-4-yl)-phenyl]-carbamic acid t-butyl ester (0.86 mmol) dissolved in 3.8 ml of abs. DMSO and 2.5 ml of t-butanol were added 139 mg of 3-anilinopropionitrile (1.1 eq.) and 116 mg of potassium t-butoxide (1.2 eq.), and the reaction was allowed to proceed for 3 hours at ambient temperature. Pouring onto crushed ice, twofold extraction with AcOEt, washing with water and brine, drying over magnesium sulfate and evaporation of the solvents left 463 mg of crude product which was used as such.
The above prepared crude condensation product was reated with 272 mg of guanidine hydrochloride (3.3 eq.), 319 mg of potassium t-butoxide (3.3 eq.) and 14 ml of ethanol and kept in an oil bath of 80° for 16 hours. The reaction mixture was then poured onto crushed ice, extracted twice with AcOEt, washed with brine, dried over magnesium sulfate and evaporated to dryness. Flash chromatography (SiO$_2$ with CH$_2$Cl$_2$/MeOH/25% NH$_3$=19/1/0.05) yielded 47 mg of the title compound as yellow solid, mp. 132° dec.
ISP MS: (MH)$^+$ 504.3. NMR: (DMSO, 1H, δ, TMS) 1.39 (s, 6H), 1.49 (s, 9H), 3.44 (s, 2H), 3.73 (s, 3H), 5.63 (br s, 2H), 5.76 (s, 1H), 6.00 (br s, 2H), 6.47 (d, J=2, 1H), 6.78 (d, J=2, 1H), 7.15 (d, J=8.5, 2H), 7.40 (s, 1H), 7.47 (d, J=8.5, 2H), 9.43 (br s, 1H).

EXAMPLE 55
5-[4-(4-Amino-phenyl)-8-ethoxy-2,2-dimethyl-2H-chromen-6-ylmethyl]-pyrimidine-2,4-diamine was prepared in analogy to example 54 but using the 8-ethoxy-derivative as starting material and cleaving the BOC-group as follows: 54 mg of {4-[6-(2,4-diamino-pyrimidin-5-ylmethyl)-B-ethoxy-2,2-dimethyl-2H-chromen-4-yl]-phenyl}-carbamic acid t-butyl ester (0.10 mmol) were dissolved in 0.8 ml of CH$_2$Cl$_2$ and treated with 0.2 ml of trifluoroacetic acid. After 3 hours the reaction mixture was poured onto crushed ice/NaHCO$_3$, extracted three times with AcOEt, the organic layer was washed with brine, dried over sodium sulfate and evaporated to dryness. Crystallization from EtOEt afforded 35 mg of the title product as brownish solid, mp. 125° dec.
ISP MS: (MH)$^+$ 418.4. NMR: (DMSO, 1H, δ, TMS) 1.29 (t, J=7, 3H),1.37 (s,6H),3.44 (s,2H),4.00 (q, J=7, 2H), 5.17 (br s, 2H), 5.55 (s, 1H), 5.64 (br s, 2H), 5.99 (br s, 2H), 6.54 (d, J=2, 1H), 6.56 (d, J=8.5, 2H), 6.75 (d, J=2, 11H), 6.93 (d, J=8.5, 2H), 7.39 (s, 1H).

EXAMPLE 56
5-[4-(3-Amino-phenyl)-8-ethoxy-2,2-dimethyl-2H-chromen-6-ylmethyl]-pyrimidine-2,4-diamine was prepared in analogy to example 55 but using (3-bromo-phenyl)-carbamic acid t-butyl ester as starting material; yellow solid, mp. 196–198° dec.
ISP MS: (MH$^+$ 418.3.

EXAMPLE 57
5-(8-Ethoxy-2,2-dimethyl-4-methylsulfanyl-2H-chromen-6-ylmethyl)-pyrimidine-2,4-diamine was prepared in analogy to example 4, but commencing the whole sequence with the, 8-ethoxy-analogue; yellow solid.
ISP MS: (MH)$^+$ 373.3.

EXAMPLE 58
5-[(8-Ethoxy-4-(2-thienyl)spiro[2H-1-benzopyran-2,1'-cyclobuten]-6-yl)methyl]-2,4-pyrimidinediamine was prepared in analogy to example 36 but using 4-bromo-8-ethoxy-spiro[2H-1-benzopyran-2,1'-cyclobutan]-6-carboxaldehyde as intermediate; yellow crystals, mp. 202°.
MS: (M)$^+$ 420, (M-C$_2$H$_4$+392.

EXAMPLE 59
5-(4-Chloro-8-ethoxy-2,2-dimethyl-2H-chromen-6-ylmethyl)-pyrimidine-2,4-diamine was prepared in analogy to example 6 but using the ethoxy-derivative as starting material; yellow crystals, mp. 197–199°.
ISP MS: (MH)$^+$ 361.2, 363.2. NMR: (DMSO, 1H, δ, TMS) 1.28 (t, J=7, 3H), 1.38 (s, 6H), 3.53 (s, 2H), 4.00 (q, J=7, 2H), 5.68 (br s, 2H), 6.03 (s, 1H), 6.08 (br s, 2H), 6.84 (d, J=2, 1H), 6.89 (d, J=2, 1H), 7.52 (s, 1H).

EXAMPLE A

| Tablets: | |
|---|---|
| Sulfamethoxazole | 400 mg |
| Compound of formula I, e.g. 5-(4-bromo-8-ethoxy-2,2-dimethyl-2H-chromen-6-ylmethyl)-pyrimidine-2,4-diamine | 80 mg |
| PRIMOJEL (starch derivative) | 6 mg |
| POVIDONE K30 (polyvinylpyrrolidone) | 8 mg |
| Magnesiumstearate | 6 mg |
| Total weight | 500 mg |

EXAMPLE B

| Tablets: | |
|---|---|
| Compound of formula I, e.g. 5-[(4-bromo-8-ethoxyspiro-[2H-1-benzopyran-2,1'-cyclobutan]-6-yl)methyl]-2,4-pyrimidinediamine | 100 mg |
| Corn starch | 15 mg |
| Talc | 3 mg |
| Magnesiumstearate | 2 mg |
| Total weight | 120 mg |

EXAMPLE C

| Injection solutions: | |
|---|---|
| Compound of formula I, e.g. 5-(8-methoxy-2,2-dimethyl-4-methylsulfanyl-2H-chromen-6-ylmethyl)-pyrimidine-2,4-diamine | 5 mg |
| Glycofurol 75 | 0.2 ml |
| Aq. bidist. sterile | ad 1.0 ml |

EXAMPLE D

| Injection solutions: | |
|---|---|
| Compound of formula I, e.g. 5-(4-bromo-8-methoxy-2,2-dimethyl-2H-chromen-6-ylmethyl)-pyrimidine-2,4-diamine | 5 mg |
| Propylene glycol | 0.5 ml |
| Aq. bidist. sterile | ad 1.0 ml |

What is claimed is:

1. A compound of the formula:

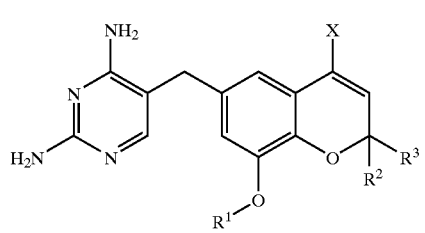

(I)

wherein
R$^1$ is alkyl or cycloalkylalkyl;
R$^2$ and R$^3$ are each independently alkyl or cycloalkyl or, taken together with the adjacent carbon atom, represent a saturated 3- to 6-membered carbocyclic or heterocyclic ring being unsubstituted or substituted; and
R$^4$ is hydrogen, halogen, cyano, alkyl, alkylthio, alkenyl, alkynyl, hydroxyalkyl, hydroxyalkynyl, alkoxyalkyl, alkoxyalkynyl, trialkylsilyl, aryl or heteroaryl;
or pharmaceutically acceptable salts thereof.

2. The compound of claim 1, wherein R$^1$ is methyl or ethyl.

3. The compound of claim 1, wherein each of R$^2$ and R$^3$ is methyl.

4. The compound of claim 1, wherein R$^2$ and R$^3$ taken together with the adjacent carbon atom represent cyclobutyl or tetrahydropyranyl.

5. The compound of claim 1, wherein R$^4$ is bromine.

6. The compound of claim 1, wherein R$^4$ is methylthio.

7. The compound of claim 1, wherein said chromene derivative is selected from the group consisting of
5-(4-bromo-8-methoxy-2,2-dimethyl-2H-chromen-6-ylmethyl)-pyrimidine-2,4-diamine,
5-[(4-bromo-2',3',5',6'-tetrahydro-8-methoxyspiro[2H-1-benzopyran-2,4'-[4H]pyran]-6-yl)-methyl]-2,4-pyrimidinediamine,
5-(8-ethoxy-2,2,4-trimethyl-2H-chromen-6-ylmethyl)-pyrimidine-2,4-diamine,
5-(4-chloro-8-methoxy-2,2-dimethyl-2H-chromen-6-ylmethyl)-pyrimidine-2,4-diamine,
5-(8-ethoxy-4-ethyl-2,2-dimethyl-2H-chromen-6-ylmethyl)-pyrimidine-2,4-diamine,
5-(8-methoxy-2,2-dimethyl-4-methylsulfanyl-2H-chromen-6-ylmethyl)-pyrimidine-2,4-diamine,
5-(8-ethoxy-2,2-dimethyl-4-propyl-2H-chromen-6-ylmethyl)-pyrimidine-2,4-diamine,
5-[8-methoxy-4-(3-methoxy-prop-1-ynyl)-2,2-dimethyl-2H-chromen-6-ylmethyl]-pyrimidine-2,4-diamine,
5-[4-(4-fluoro-phenyl)-8-methoxy-2,2-dimethyl-2H-chromen-6-ylmethyl]-pyrimidine-2,4-diamine,
5[(4-bromo-8-ethoxyspiro[2H-1-benzopyran-2,1'-cyclobutan]-6-yl)methyl]-2,4-pyrimidinediamine, and
5-[4-bromo-8-ethoxy-2,2-dimethyl-2H-chromen-6-lymethyl)-pyrimidine-2,4-diamine.

8. A method for making a compound of formula (I) according to claim 1, comprising:
reacting a compound of the formula (II)

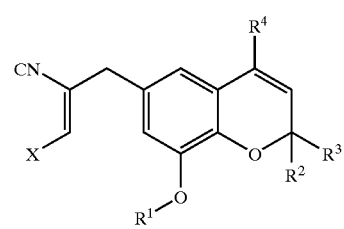

(II)

wherein R$^1$, R$^2$, R$^3$, and R$^4$ are as defined in claim 1 and X is a leaving group, with a guanidine or a salt thereof to make the compound of formula (I) of claim 1.

9. The method according to claim 8, further comprising:
protecting at least one functional group prior to the reaction with said guanidine or said salt thereof; and
cleaving said protecting group to give said compound of formula (I).

10. A method for making a compound of formula (I) of claim 1, comprising:

reacting a compound of formula (Ia)

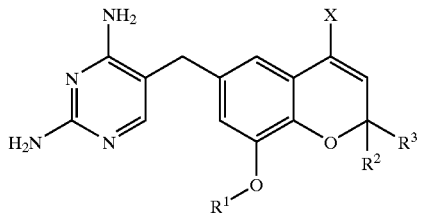

(Ia)

wherein $R^1$, $R^2$, $R^3$, and $R^4$ are as defined in claim 1, provided that $R^4$ is neither a hydrogen atom nor a halogen atom with a compound of the formula (III)

$$R^4 Y \qquad (III)$$

wherein one of X and Y represents a leaving group and the other of X and Y represents a group which is eliminated with this leaving group, to make the compound of formula (I) of claim 1.

11. A pharmaceutical composition comprising a pharmaceutically effective amount of a compound of formula (I)

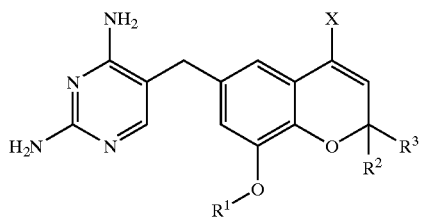

(I)

wherein
- $R^1$ is alkyl or cycloalkylalkyl;
- $R^2$ and $R^3$ are each independently alkyl or cycloalkyl or, taken together with the adjacent carbon atom, represent a saturated 3- to 6-membered carbocyclic or heterocyclic ring being unsubstituted or substituted; and
- $R^4$ is hydrogen, halogen, cyano, alkyl, alkylthio, alkenyl, alkynyl, hydroxyalkyl, hydroxyalkynyl, alkoxyalkyl, alkoxyalkynyl, trialkylsilyl, aryl or heteroaryl;

or pharmaceutically acceptable salts thereof; and a pharmaceutically acceptable carrier.

* * * * *

UNITED STATES PATENT AND TRADEMARK OFFICE
CERTIFICATE OF CORRECTION

PATENT NO.         : 6,818,649 B2                              Page 1 of 2
APPLICATION NO. : 10/258777
DATED              : November 16, 2004
INVENTOR(S)        : Mohr et al.

It is certified that error appears in the above-identified patent and that said Letters Patent is hereby corrected as shown below:

Claim 1, line 2 of the claim, please change the formula:

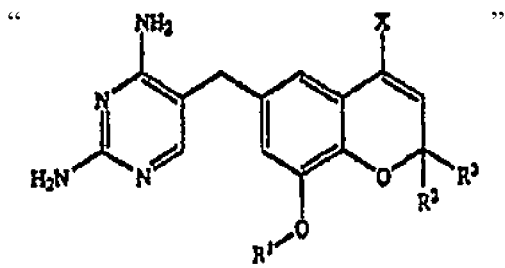

to read

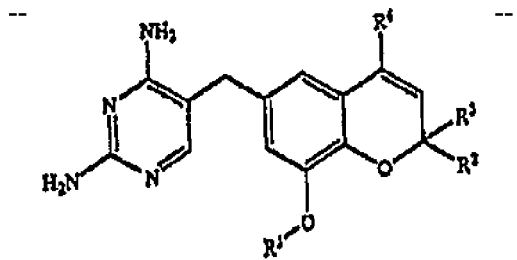

UNITED STATES PATENT AND TRADEMARK OFFICE
CERTIFICATE OF CORRECTION

PATENT NO. : 6,818,649 B2
APPLICATION NO. : 10/258777
DATED : November 16, 2004
INVENTOR(S) : Mohr et al.

It is certified that error appears in the above-identified patent and that said Letters Patent is hereby corrected as shown below:

Claim 11, line 3 of the claim, please change the formula:

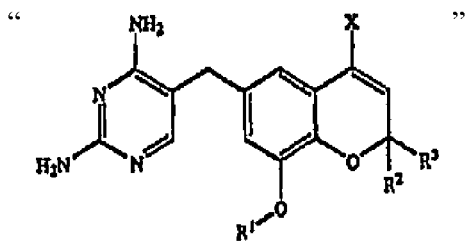

to read

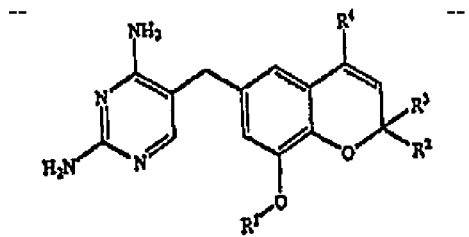

Signed and Sealed this

Eighteenth Day of September, 2007

JON W. DUDAS
*Director of the United States Patent and Trademark Office*